US012616777B2

(12) United States Patent
Taton et al.

(10) Patent No.: US 12,616,777 B2
(45) Date of Patent: *May 5, 2026

(54) SILICONE POLYUREA BLOCK COPOLYMER COATING COMPOSITIONS AND METHODS

(71) Applicant: Innovative Surface Technologies, Inc., St. Paul, MN (US)

(72) Inventors: Kristin Taton, Little Canada, MN (US); Patrick Guire, Hopkins, MN (US); Charles Leir, Ironton, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 480 days.

This patent is subject to a terminal disclaimer.

(21) Appl. No.: 18/133,259

(22) Filed: Apr. 11, 2023

(65) Prior Publication Data

US 2023/0241287 A1 Aug. 3, 2023

Related U.S. Application Data

(63) Continuation of application No. 16/771,380, filed as application No. PCT/US2018/064988 on Dec. 11, 2018, now Pat. No. 11,672,884.

(60) Provisional application No. 62/597,168, filed on Dec. 11, 2017.

(51) Int. Cl.

| | |
|---|---|
| ***A61L 27/00*** | (2006.01) |
| ***A61L 27/34*** | (2006.01) |
| ***A61L 31/10*** | (2006.01) |
| ***C08G 18/61*** | (2006.01) |
| ***C08G 18/64*** | (2006.01) |
| ***C08G 18/73*** | (2006.01) |
| ***C08G 18/75*** | (2006.01) |
| ***C08G 18/77*** | (2006.01) |
| ***C09D 183/10*** | (2006.01) |

(52) U.S. Cl.

CPC ............... *A61L 27/34* (2013.01); *A61L 31/10* (2013.01); *C08G 18/61* (2013.01); *C08G 18/6423* (2013.01); *C08G 18/73* (2013.01); *C08G 18/757* (2013.01); *C08G 18/778* (2013.01); *C09D 183/10* (2013.01); *C08G 2150/00* (2013.01)

(58) Field of Classification Search

CPC ......... A61L 27/34; A61L 31/10; C08G 18/61; C08G 18/6423; C08G 18/73; C08G 18/757; C08G 18/778; C08G 2150/00; C09D 183/10

USPC ..................................................... 106/287.11

See application file for complete search history.

(56) References Cited

U.S. PATENT DOCUMENTS

| | | | | |
|---|---|---|---|---|
| 5,214,119 | A | 5/1993 | Leir et al. | |
| 5,290,615 | A | 3/1994 | Tushaus et al. | |
| 5,461,134 | A | 10/1995 | Leir et al. | |
| 5,512,650 | A | 4/1996 | Leir et al. | |
| 5,670,598 | A | 9/1997 | Leir et al. | |
| 5,759,695 | A | 6/1998 | Primeaux, II | |
| 5,792,554 | A | 8/1998 | Leir et al. | |
| 6,013,755 | A | 1/2000 | Primeaux, II et al. | |
| 6,824,820 | B1 | 11/2004 | Kinning et al. | |
| 11,672,884 | B2 * | 6/2023 | Taton .................. | C09D 183/10 106/287.11 |
| 2006/0210807 | A1 | 9/2006 | Miller | |
| 2008/0127429 | A1 | 6/2008 | Brun et al. | |
| 2008/0171010 | A1 | 7/2008 | Brun | |
| 2010/0247904 | A1 | 9/2010 | Larson et al. | |
| 2011/0076795 | A1 | 3/2011 | Schaefer et al. | |

FOREIGN PATENT DOCUMENTS

| | | | | |
|---|---|---|---|---|
| EP | 0068385 | A1 | 1/1983 | |
| WO | 199630426 | A1 | 10/1996 | |
| WO | WO-9630426 | A1 * | 10/1996 | ........... C08G 77/458 |
| WO | 2006034411 | A2 | 3/2006 | |
| WO | 2009064879 | A2 | 5/2009 | |
| WO | 2019118483 | A1 | 6/2019 | |

OTHER PUBLICATIONS

Extended European Search Report for corresponding European Patent Application No. EP 18889122 dated Jul. 23, 2021, pp. 1-2.
International Search Report for corresponding International Application No. PCT/US2018/064988 dated Feb. 19, 2019, pp. 1-2.

* cited by examiner

*Primary Examiner* — James E McDonough
(74) *Attorney, Agent, or Firm* — Weaver Legal and Consulting LLC

(57) ABSTRACT

Silicone polyurea block copolymers are prepared by copolymerizing: (a) a diamine composition that includes a polyethylene glycol diamine, and optionally, a dipiperidyl alkane; (b) a monofunctional silicone isocyanate; and (c) a diisocyanate. Compositions useful as passivating coatings comprising the block copolymer are also provided, and substrates coated with the compositions. Methods of preparing and using the compositions are also described.

20 Claims, No Drawings

SILICONE POLYUREA BLOCK COPOLYMER COATING COMPOSITIONS AND METHODS

CROSS REFERENCE TO RELATED APPLICATIONS

This application is a continuation of U.S. application Ser. No. 16/771,380, filed Jun. 10, 2020, which is a U.S. National Stage under 35 U.S.C. 371 of PCT Application No. PCT/US2018/064988, filed Dec. 11, 2018, which claims benefit under 35 U.S.C. 119(e) to U.S. Provisional Patent Application Ser. No. 62/597,168, entitled, "Silicone Polyurea Block Copolymer Coating Compositions and Methods," and filed Dec. 11, 2017, the contents of which are incorporated herein in their entirety for all purposes.

FIELD OF THE INVENTION

Block copolymers having an A-B-A structure, with A being a silicone segment linked to the B segment through a urea linkage. The B segment is comprised of a random copolymer block of C-D repeating monomers linked through a urea group, where C is a hydrocarbon having 2 to 20 carbon atoms, and D is a polyethylene glycol/polypropylene glycol copolymer or dipiperidyl propane. The block copolymers are prepared by reacting monofunctional silicone isocyanate with diamines and diisocyanates. The silicone polyurea block copolymers thus formed can be utilized in coating compositions for application to surfaces, particularly surfaces that come in contact with aqueous environments and/or biological fluids, such as medical devices and diagnostics. The silicone polyurea copolymers can provide advantageous features to a surface. Articles are also described that include the coating compositions on a surface, as well as methods to coat surfaces.

BACKGROUND

Silicone rubber surfaces are known for excellent biocompatibility and reduced non-specific protein and cell adhesion over other surfaces, when such surfaces are exposed to biological fluids (for example, when emplaced, either temporarily, for extended periods of time, or permanently, in a patient's body). However, silicone is not suitable for the bulk material of many devices utilized in the medical field, for example, implantable devices, devices for in vitro diagnostics, and/or devices that come in contact with biological fluids outside a patient's body or temporarily emplaced within a patient's body. This unsuitability is due in large part to the material's high elasticity.

Medical devices and diagnostic products are frequently made from temperature sensitive materials that can be easily damaged by many solvents. Ideally, therefore, a coating to be applied to such devices and diagnostic products would be soluble in water, or in a less aggressive solvent such as an alcohol. One solvent used when applying coatings to medical devices and diagnostics is isopropanol, and this solvent is generally accepted by the industry.

BRIEF SUMMARY OF THE INVENTION

Silicone polyurea block copolymers, coating compositions including these block copolymers, methods of synthesizing the block copolymers, methods of providing a passivating or a lubricious surface using the block copolymers, and coated surfaces are described herein. Silicone polyurea copolymers include siloxane, alkyl, and polyethylene glycol/polypropylene glycol copolymer or dipiperidyl propane repeating units separated by urea linkages. In some implementations, the total isocyanate ("total isocyanate" as used herein to include mono- and diisocyanate) is present in a molar ratio with total diamines in a range of 1.5:1 to 1.05:1, or in a range of 1:1.05 to 1:1, or in a range of 1.3:1 to 1.2:1, or in a range of 1:1.2 to 1:1.3. In some implementations, total isocyanate is present in an amount that is equal to, or greater than, the amount of total diamines in the silicone polyurea block copolymer.

Inventive silicone polyurea copolymers can provide a wide variety of properties to a surface. In some implementations, inventive silicone polyurea copolymers provide passivating surfaces or lubricious surfaces to medical devices and diagnostics. The silicone polyurea copolymers can exhibit improved properties as compared to other polymers used to modify surface properties of a device. In particular, inventive silicone polyurea copolymers can be synthesized under relatively simple reaction conditions, and the resulting block copolymers can be soluble in mild solvents (e.g., water, alcohol, alcohol-water mixtures, or buffer solutions), can be easily applied to a wide variety of surfaces, and are customizable for particular applications.

In some aspects, inventive polyurea copolymers can provide antifouling coating compositions that are suitable for use as coatings on articles immersed in or exposed to an aquatic environment (referred to herein as "aquatic articles). Aquatic environments encompass natural or artificial systems such as lakes, rivers, fountains, ponds (e.g., fish ponds), canals, aquariums, aquaculture systems, water holding or conveying systems, water reservoirs, open drinking water systems, brackish water environments, waste water and oceans. In these aspects, inventive polyurea copolymers can be used in connection with man-made structures such as docks, ship and boat hulls, buoys, drilling platforms, oil production rigs, and pipes that are immersed in water that are prone to fouling by aquatic organisms such as green and brown algae, barnacles, mussels, and the like.

In some implementations, silicone polyurea block copolymers are provided that are pre-formed, fully polymerized, customizable polymers that are soluble in water, alcohol, alcohol-water mixtures, or buffer solutions. In this sense, inventive silicone polyurea block copolymers are provided wherein no further polymerization is required to provide the desired characteristics of solubility, passivity, durability, molecular weight, viscosity, and the ability to attach to a surface via physisorption. This is in contrast to prepolymers, which generally refer to a starting polymer that has been reacted to an intermediate molecular mass state, and that can be further polymerized by reactive groups to a fully cured state that has a molecular weight much higher than the starting polymer.

In some implementations, the pre-formed, fully polymerized, customizable polymers comprise linear copolymers, i.e., a continuous chain of repeat units (the copolymer backbone). In some aspects, inventive silicone polyurea block copolymers can have a relatively low molecular weight, for example, inventive silicone polyurea copolymers can have an average molecular weight of 100,000 or less, or 90,000 or less, or 80,000 or less, or 70,000 or less, or 60,000 or less, or 50,000 or less, or 40,000 or less, or 30,000 or less, or 20,000 or less, or an average molecular weight in a range of about 5,000 to about 100,000, or about 5,000 to about 90,000, or about 5,000 to about 80,000, or about 5,000 to about 70,000, or about 5,000 to about 60,000, or about 5,000 to about 50,000, or about 5,000 to about 40,000, or about 5,000 to about 30,000, or about 5,000 to about 20,000, or about 10,000 to about 15,000. Use of difunctional monomers (diamines and diisocyanates) that have molecular weights in specified ranges can allow the user to control the molecular weight and linear architecture of the final, preformed copolymer. In some aspects, control of molecular weight can have an impact on solubility of the silicone polyurea copolymer.

In some implementations, inventive concepts provide a coating composition for a surface, such as the surface of a medical device or marine article, the coating composition comprising a silicone polyurea copolymer comprising a reaction product of:

(a) a diamine composition comprising a poly(ethylene glycol) diamine having a formula (I), (II), or a combination of diamines of formulae (I) and (II):

(I)

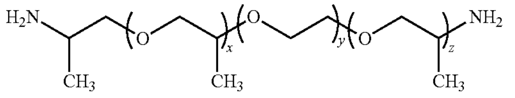

wherein y is an integer in the range of 2 to 40, and x+z is an integer in the range of 1 to 8; and (II)

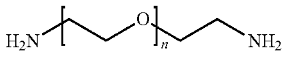

wherein n is an integer in the range of 1 to 500;

(b) a monofunctional silicone isocyanate having a formula:

(VIII)

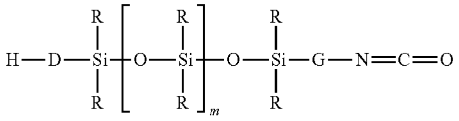

wherein D is an alkyl radical having 1 to 6 carbon atoms,

G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (c) a diisocyanate, wherein total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III):

(III)

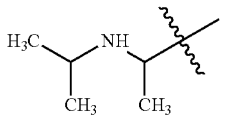

In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV):

(IV)

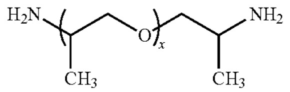

wherein x is an integer in the range of 2 to 70; or a poly(ethylene glycol) diamine having a formula (V):

(V)

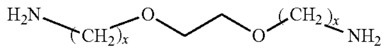

wherein x is 2 or 3.

Thus, in some aspects, the diamine composition (a) can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including the JEFFAMINE® D, ED, EDR and SD series.

In some implementations, the coating composition can be a passivator. In other implementations, the coating composition can be a primer, wherein one or more additional coating layers are provided to the coating composition after it has been associated with a surface. In these aspects, additional coating layers can provide desirable properties to the coated surface, such as antimicrobial properties or the like.

Implementations can include any or all of the following features. The diamine composition of (a) can further include a dipiperidyl alkane, wherein the diamine combination comprises 20 to 99.9 molar percent of the polyethylene glycol and 0.1 to 80 molar percent of the dipiperidyl alkane. The polyethylene glycol diamine can have a molecular weight of about 100 to about 35,000, or about 100 to about 25,000, or about 100 to about 10,000, or about 500 to about 25,000, or about 500 to about 10,000, or about 500 to about 5,000. The dipiperidyl alkane can have a formula:

(VI)

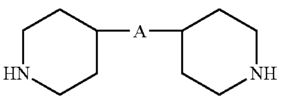

where A is a C0 to C8 bivalent alkyl radical. In some aspects, the dipiperidyl alkane comprises dipiperidyl propane.

In some implementations, the silicone isocyanate can have a molecular weight in a range of 1,000 to 20,000.

In some aspects, the diisocyanate has a formula:

OCN—B—NCO (VII)

where B is a bivalent alkyl radical having 2 to 20 carbon atoms. The diisocyanate can be selected from hexane diisocyanate and isophorone diisocyanate.

In some aspects, the silicone polyurea copolymer can comprise polyethylene glycol in amount of 25 to 95 weight percent, based on total weight of the silicone polyurea copolymer.

Optionally, inventive silicone polyurea copolymers can include latent reactive groups and/or biomolecules. In these aspects, latent reactive groups and/or biomolecules can provide customizable copolymers, wherein the end user can attach additional components based upon the ultimate use of the copolymers. In some implementations, latent reactive groups can be utilized to attach additional coating layers (such as topcoat layers) to a surface. In these instances, the silicone polyurea copolymer coating layer can act as a priming layer for attachment of additional desired coating layers. In some aspects, latent reactive groups can provide improved durability of the copolymers, when applied to a surface.

Illustrative latent reactive groups include photoreactive, thermally reactive, and/or chemically reactive groups as discussed herein. Illustrative biomolecules include avidin (including streptavidin), hyaluronic acid, heparin, haptens, antibodies, and the like. Suitable dyes include, for example, fluorescent dyes such as fluorescein isothiocyanate (FITC), coumarin, Alexa Fluor, Cy3, Cy5, Oregon Green, Pacific Blue, Pacific Green, Pacific Orange, tetramethylrhodamine (TRITC), Texas Red, and the like.

Other features can include the following. The silicone polyurea copolymer can be provided in solution in water, alcohol, an alcohol-water mixture, and/or a buffer. Thus, in some aspects, inventive concepts provide a composition comprising:

(a) a solvent selected from water, alcohol, an alcohol-water mixture, or a buffer; and (b) a silicone polyurea copolymer in solution, the silicone polyurea copolymer comprising a reaction product of:

(i) a diamine composition comprising a poly(ethylene glycol) diamine having a formula (I), (II), or a combination of diamines of formulae (I) and (II):

(I)

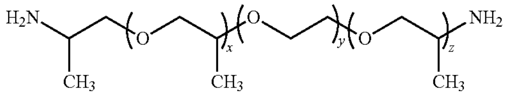

wherein y is an integer in the range of 2 to 40, and x+z is an integer in the range of 1 to 8; and (II)

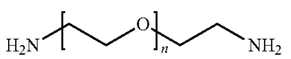

wherein n is an integer in the range of 1 to 500;

(ii) a monofunctional silicone isocyanate having a formula:

(VIII)

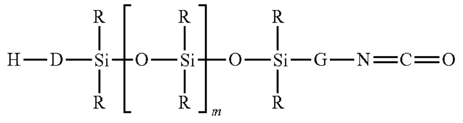

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (iii) a diisocyanate, wherein total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III) as represented above. In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV) or a poly(ethylene glycol) diamine having a formula (V) represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including the JEFFAMINE® D, ED, EDR and SD series.

The silicone polyurea block copolymer solution can be put to a wide variety of uses, as will be apparent upon review of the present description.

In some aspects, the surface to which the coating composition is applied can be a surface that contacts biological fluids. The surface can be a surface of an implantable medical device, a medical device for temporary insertion into a patient's body, devices that contact biological fluids outside a patient's body (such as tubing or the like), or an in vitro diagnostic device. In other aspects, the surface to which the coating composition is applied can be a surface exposed to aqueous conditions for extended periods of time. The surface can be fabricated from a wide variety of materials, such as metal, polymer, ceramic, glass, fabric or biomaterial.

In a further aspect, a medical device is provided having a surface containing a passivating coating, the passivating coating comprising a silicone polyurea copolymer that is a reaction product of:

(a) a diamine composition comprising a polyethylene glycol diamine having a formula (I), (II), or a combination of (I) and (II):

(I)

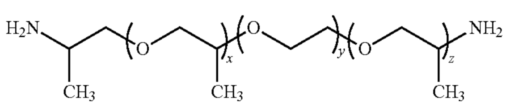

wherein y is an integer in the range of 2 to 40, and x+z is an integer in the range of 1 to 8; or (II)

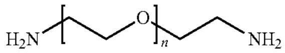

wherein n is an integer in the range of 1 to 100;

(b) a monofunctional silicone isocyanate having a formula:

(VIII)

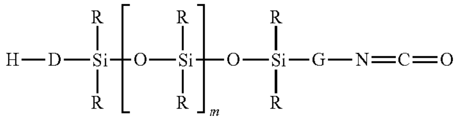

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (c) a diisocyanate, wherein total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III) as represented above. In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV) or a poly(ethylene glycol) diamine having a formula (V) represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including the JEFFAMINE® D, ED, EDR and SD series.

Inventive silicone polyurea copolymers, and coating compositions including these copolymers, can be provided to a wide variety of medical devices and diagnostics.

In still further aspects, methods for forming a passivating coating on a surface of a medical device comprise steps of:

(a) Providing a silicone polyurea copolymer solution comprising a reaction product of (i) a diamine composition comprising a polyethylene glycol diamine having a formula (I), (II), or a mixture of (I) and (II):

(I)

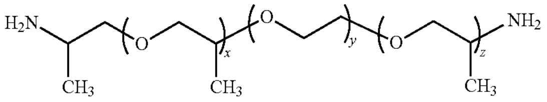

wherein y is an integer in the range of 2 to 40, and x+z is an integer in the range of 1 to 8; or (II)

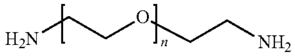

wherein n is an integer in the range of 1 to 500; (ii) a monofunctional silicone isocyanate having a formula:

(VIII)

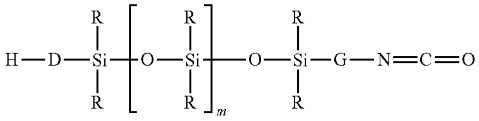

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (iii) a diisocyanate, wherein total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III) as represented above. In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV) or a poly(ethylene glycol) diamine having a formula (V) represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including the JEFFAMINE® D, ED, EDR and SD series.

Inventive silicone polyurea block copolymers, and coating compositions including these copolymers, can be provided to a wide variety of medical devices and diagnostics. In some embodiments, inventive silicone polyurea copolymers can be applied to surfaces of microbeads, ophthalmic devices, neurological devices, and the like. In some aspects, the silicone polyurea block copolymers can be uncrosslinked.

In still further aspects, methods for forming a passivating coating on a surface of a medical device comprise steps of:

(a) Providing a silicone polyurea block copolymer solution comprising a reaction product of (i) a diamine composition comprising a polyethylene glycol diamine having a formula (I), (II), or a combination of (I) and (II):

(I)

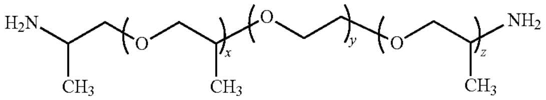

wherein y is an integer in the range of 2 to 40, and x+z is an integer in the range of 1 to 8; or (II)

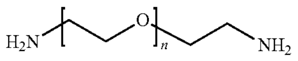

wherein n is an integer in the range of 1 to 100;

(ii) a monofunctional silicone isocyanate having a formula:

(VIII)

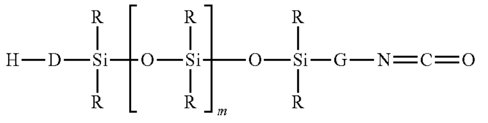

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (iii) a diisocyanate, wherein total isocyanate is present in a molar ratio with total diamines in (i) in a range of 1.5:1 to 1.05:1, the solution being provided in water, an alcohol, or an alcohol-water mixture;

(b) Covering the surface of the medical device with the silicone polyurea copolymer solution; and (c) Removing the silicone polyurea copolymer solution from the surface.

The molar ratio of total isocyanate to total diamines can be in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III) as represented above. In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV) or a poly(ethylene glycol) diamine having a formula (V) represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including the JEFFAMINE® D, ED, EDR and SD series.

The diamine composition of (i) can further comprise a dipiperidyl alkane, wherein the diamine composition comprises 20 to 99.9 molar percent of the polyethylene glycol and 0.1 to 80 molar percent of the dipiperidyl alkane. Step (b) can comprise spraying the aqueous silicone polyurea copolymer solution onto the surface or dipping the surface into the aqueous silicone polyurea copolymer solution. Step (c) can comprise rinsing the surface with an aqueous solution. In some implementations, methods do not require a curing step, but rather yield biocompatible passivating properties upon drying at room temperature.

In some aspects, inventive silicone polyurea block copolymers can provide one or more of the following advantageous features. The A-B-A silicone polyurea copolymer coating can provide strong adherence to a substrate of choice, even when such substrate is fabricated from a material other than silicone. Inventive silicone polyurea copolymers can provide excellent biocompatibility and reduced non-specific protein and cell adhesion over other similar surfaces that do not contain the copolymer. Coatings formed by the silicone polyurea copolymers can provide passivation against biomolecules, thereby reducing foreign body response and inflammation due to short-term and long-term implantable medical devices. The silicone polyurea block copolymers can be easily applied to a wide variety of substrate surfaces, and in some embodiments, the coating does not require a curing step when applied to such substrate surfaces. Inventive silicone polyurea copolymers can provide customizable copolymers, where choice of diamine(s), monofunctional silicone isocyanate(s) and/or diisocyanate(s) can modify the mechanical properties of the polymer when coated on a surface. Other characteristics that can be tailored based upon selection of diamine(s), monofunctional silicone isocyanate(s) and/or diisocyanate(s) include release characteristics, gas permeability, hydrophobicity and lubricity.

In further implementations, inventive concepts include methods for preparing novel silicone polyurea copolymers, methods including combining, under suitable reaction conditions, the following:

(i) a diamine composition comprising a polyethylene glycol diamine having a formula (I), (II), or a mixture of (I) and (II):

(I)

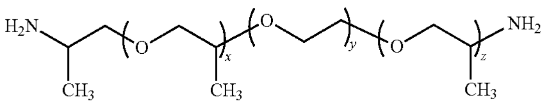

wherein y is an integer in the range of 2 to 40, and x+z is an integer in the range of 1 to 8; or (II)

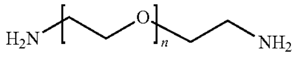

wherein n is an integer in the range of 1 to 100;

(ii) a monofunctional silicone isocyanate having a formula:

(VIII)

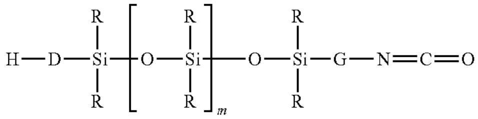

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (iii) a diisocyanate, wherein total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3. Reactants can be combined in solvents such as water, an alcohol, or an alcohol-water mixture.

In some implementations, the diamine composition of (i) comprises a secondary amine version of the poly(ethylene glycol) diamine of formula (I), in which the amine end-groups are reacted with a ketone (e.g., acetone) and reduced to create hindered secondary amine end groups represented by the terminal structure represented by formula (III) as represented above. In these aspects, one reactive hydrogen on each end group provides for more selective reactivity. These embodiments can be useful for intermediate synthesis and intrinsically slower reactivity compared primary amines.

In some implementations, the diamine composition of (i) comprises a poly(propylene glycol) diamine having a formula (IV) or a poly(ethylene glycol) diamine having a formula (V) represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including the JEFFAMINE® D, ED, EDR and SD series.

Optionally, the diamine composition can further include a dipiperidyl alkane, wherein the diamine composition comprises 20 to 99.9 molar percent of the polyethylene glycol and 0.1 to 80 molar percent of the dipiperidyl alkane. The dipiperidyl alkane can have a formula:

(VI)

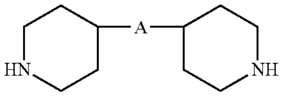

where A is a C0 to C8 bivalent alkyl radical. In some aspects, the dipiperidyl alkane comprises dipiperidyl propane.

It will be readily appreciated that inventive silicone polyurea block copolymer compositions can be used to provide a passivating coating on surfaces that are exposed to aqueous conditions for extended periods of time, such aquatic articles including, for example, water treatment system components (vessels, tanks, containers, filters, membranes, pipes, and the like), condenser coils, and/or marine vessels (such as boat or ship hulls, tanks, docks and the like), and marine vessel components (such as motors, anchors, rudders, and the like). Inventive silicone polyurea copolymers can provide antifouling coating compositions on articles immersed or exposed to an aquatic environment. Such silicone polyurea block copolymer compositions, methods of coating, and coated articles, can apply the principles described herein.

Advantageously, condensation polymerization of these reactants can take place under simplified reaction conditions. In some implementations, the condensation reaction can take place at room temperature, or at a temperature in a range of about 20° C. to about 25° C. In some aspects, the reaction can be mildly heated to temperatures below 100°; in some implementations, temperature need not be controlled during the reaction. In some implementations, the condensation reaction does not require an inert atmosphere and/or controlled pressure conditions. In some embodiments, inventive silicone polyurea copolymers can be formed by condensation polymerization under ambient room conditions (gas, temperature, pressure and/or humidity).

Inventive concepts also include silicone polyurea block copolymers that comprise a random copolymer with alternating diisocyanate/diamine segments. The block copolymers have an A-B-A structure, with A being a silicone segment linked to the B segment through a urea linkage. The B segment is comprised of a random copolymer block of C-D repeating monomers linked through a urea group, where C is a hydrocarbon having 2 to 20 carbon atoms, and D is a polyethylene glycol/polypropylene glycol copolymer or dipiperidyl propane, where at least 20 molar % is polyethylene glycol/polypropylene glycol and up to 80 molar % is dipiperidyl propane.

DETAILED DESCRIPTION

Inventive silicone polyurea block copolymers comprise polymerization products of the condensation reaction of suitable di-functional amine monomer(s) with suitable di-functional isocyanate monomer(s) and monofunctional silicone isocyanate. The di-functional monomers provide multiple urea linkages [—$R^a$N—(CO)—N$R^b$—] between polyethylene glycol and hydrocarbon segments of the copolymer, where (CO) defines a carbonyl group C═O, and each $R^a$ and $R^b$ is independently a hydrogen or an alkyl group. Diamine compositions used to form the silicone polyurea copolymers include polyethylene glycol diamines and, optionally, dipiperidyl alkanes. When the diamine(s) and diisocyanate(s) condense to form a lengthening polyurea chain, reaction with a monofunctional silicone isocyanate terminates the polymerization.

The resulting compound is a triblock A-B-A copolymer wherein A comprises the silicone terminal segment; B comprises C-D repeating monomers linked through a urea group, where C is a hydrocarbon having 2 to 20 carbon atoms, and D is a polyethylene glycol/polypropylene glycol copolymer or dipiperidyl propane; wherein each "-" represents a urea linkage. Thus, in context of the present disclosure, the term "silicone polyurea" will be used to refer to these polymerization products.

These silicone polyurea copolymers can provide good mechanical and adhesive properties due to the hard segment (polyurea). Urea linkages can provide improved adhesion through hydrogen bonding, and the choice of diamine(s) and diisocyanate(s) can modify the mechanical properties of the polymer when coated on a surface. The soft segment of the copolymer (silicone) can provide good release characteristics, gas permeability, biocompatibility and/or lubricity.

In accordance with inventive concepts, incorporating a terminal silicone segment within the copolymer is designed to simulate the properties of a silicone surface. As the silicone polyurea copolymer dries on a surface, silicone blocks will tend to arrange at the air interface due to their hydrophobicity. Low molecular weight silicones migrate to the surface of coatings partially due to this effect. Placing the silicone block at the termini of the copolymer, as in an A-B-A copolymer, can increase the likelihood that the silicone is free to move to the surface in a larger copolymer molecule. In some aspects, a copolymer with a Tg higher than about 25° C. to 50° C. will be effectively "locked" in a configuration with the silicone blocks exposed on the outermost surface when dried in air.

For purposes of discussion herein, the silicone polyurea copolymers are described as having a polymer backbone chain and two end-groups. In accordance with inventive concepts herein discussed, the polymer backbone has the following characteristics: consists of the longest series of covalently bonded atoms that together create the continuous chain of the copolymer; is the linear sequence of constitutional units to which all other chains, long or short or both, may be regarded as being pendant; and exists between two boundary constitutional units, each of which is referred to as an end-group. In some aspects, silicone polyurea block copolymers are linear (unbranched).

The reaction to produce the inventive silicone polyurea copolymers involves mixing under reactive conditions the di-functional amine(s), monofunctional silicone isocyanate, and di-functional isocyanate(s) under reactive conditions to produce a silicone polyurea copolymer having desired surface properties (e.g., wet or dry lubricity, passivation, etc.).

In some implementations, molecular weight of the silicone polyurea block copolymer is controlled. In some aspects, average molecular weight of the silicone polyurea copolymer can be 100,000 or less, or 90,000 or less, or 80,000 or less, or 70,000 or less, or 60,000 or less, or 50,000 or less, or 40,000 or less, or 30,000 or less, or 20,000 or less, or an average molecular weight in a range of about 5,000 to about 100,000, or about 5,000 to about 90,000, or about 5,000 to about 80,000, or about 5,000 to about 70,000, or about 5,000 to about 60,000, or about 5,000 to about 50,000, or about 5,000 to about 40,000, or about 5,000 to about 30,000, or about 5,000 to about 20,000, or about 10,000 to about 15,000. Molecular weight can be controlled, for example, by controlling the size and ratios of monomers. Since monomers used are diamines, isocyanates and diisocyanates, monomers react via condensation to form the copolymer. The relatively low molecular weight of inventive silicone polyurea copolymers can provide excellent solubility properties. Molecular weight can be adjusted to provide the desired solubility, considering starting monomers and the solvent used with the silicone polyurea copolymer end product.

In some implementations, the silicone polyurea polymerization reaction is in a molar ratio of total isocyanate to total amines in a range of 1.5:1 to 1.05:1. The molecular weight of the resulting polymer can be controlled by the ratio of the two reactants. If one reactant is in excess, the other reactant will be the limiting reagent. As the ratio of excess increases, the molecular weight decreases because there is an insufficient molar amount of the limiting reagent to continue polymerization. For instance, if the feed ratio of the reaction is 1.3:1 total isocyanate to total diamine, the polymer will still contain alternating monomers from the diisocyanate and diamine linked by the urea, but both ends of the polymer will be isocyanate terminated and the length will be a statistical distribution determined theoretically by the ratio. The Carothers equation describes this state for a linear polymer with two monomers, where the limiting monomer is completely reacted as the number average of degree of polymerization $X_n$ as:

$$X_n=(1+r)/(1-r)$$

where r is (molar ratio of monomer A)/(molar ratio of monomer B) where monomer B is in excess (e.g., for 1.3:1 r=0.77)

For 30% excess monomer, the degree of polymerization is 7.7 versus infinity for the perfectly 1:1 equimolar case. For 10% excess monomer, the degree of polymerization is 21. The degree of polymerization specifies the average number of monomer units in a polymer and can be converted to molecular weight by multiplying by the monomer weights. Therefore, the molecular weight can be controlled by altering the excess monomer ratio in the polymerization reaction. Similarly, molecular weight is a factor in solubility, with molecular weight typically inversely proportional to solubility of a polymer in a given solvent. Altering the monomer ratio can therefore increase solubility of the resulting silicone polyurea.

The Carother's equation above assumes that conversion of the monomers is complete and that there is no terminating monomer present. With the silicone mono-isocyanate present as a chain terminator, it serves to further decrease the degree of polymerization and therefore the molecular weight of the polymer. The more silicone mono-isocyanate is present, the lower the degree of polymerization. If a mono-functionalized monomer is present it can be factored into the Carother's equation as r=molar ratio monomer A/(molar ratio monomer B+2×molar ratio monomer C) where A is the monomer with the lower amount, B is the higher amount monomer, and C is the mono-functional monomer. For example, if there is 1 mole % silicone monoisocyanate and equal molar amounts of diamine and diisocyanate, the r value is 0.98 and the degree of polymerization is 99. If these effects are combined, with a molar excess of 30% and 1% of silicone monoisocyanate the r value is 0.76, and the degree of polymerization is 7.3. Both molar excess and amount of chain terminating mono-functional monomer affect the degree of polymerization and molecular weight. The effect of difunctional monomer molar excess can be easier to control than the monofunctional monomer amount because typically monofunctional silicone monomers are less commercially available, costlier, and can possess different solubility.

In some aspects, inventive polyurea copolymers contain relatively few repeating units of the di-functional amine monomer(s) and di-functional isocyanate monomer(s), given the reactivity of these starting materials. Thus, in some implementations, inventive polyurea copolymers can be considered oligomers, in that the structure of the copolymers essentially comprises a small plurality of units derived from molecules of lower relative molecular mass. For example, silicone polyurea copolymers in accordance with inventive principles can include less than 40, or less than 30, or less than 20, or less than 10, or less than 9, or less than 8, or less than 7, or less than 6, or less than 5, or less than 4, or even 3 monomeric units. Such oligomeric species can be present within the polyurea copolymer reaction product, for example, in an amount up to about 25% of the total product. The presence of smaller molecular weight species may provide advantages, for example, for ease of manufacturing and/or solubility of the copolymer.

When the silicone polyurea is formed with very close to the 1:1 molar ratio of total isocyanate:total amine in the reaction mixture, the resulting polymer can have very high molecular weight. Depending on the monomers chosen, in some cases, the high molecular weight polymer has a viscosity that can make it difficult to dissolve and coat out of alcohols and other solvents. Lower molecular weight silicone polyureas have better solubility in alcohols. In some cases, a molar ratio of total isocyanates:total amines in a range of 1.5:1 to 1.05:1, or in a range of 1:1.05 to 1:1.5 can be preferred, and a ratio in a range of 1.3:1 to 1.2:1, or 1:1.2 to 1:1.3 can be particularly preferred.

Suitable reaction solvents are those which are unreactive with the mono- and diisocyanate(s) and which maintain the reactants and products in solution throughout the polymerization reaction. Useful reaction solvents include alcohol (such as isopropanol and methanol), tetrahydrofuran (THF), ethers, ethyl acetate, dimethyl sulfoxide (DMSO), dimethylformamide (DMF), acetone, methyl ethyl ketone, chloroform, dichloromethane, and other common organic solvents. Typical reaction conditions are illustrated in the Examples.

Turning to inventive compositions, in a first aspect, a coating composition for a surface comprises a silicone polyurea copolymer comprising a reaction product of:

(a) a diamine composition comprising a poly(ethylene glycol) diamine having a formula (I), (II), or a combination of diamines of formulae (I) and (II):

(I)

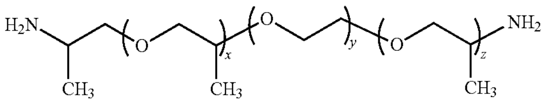

wherein y is an integer in the range of 2 to 40, and x+z is an integer in the range of 1 to 8; and (II)

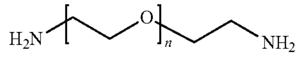

wherein n is an integer in the range of 1 to 500;

(b) a monofunctional silicone isocyanate having a formula:

(VIII)

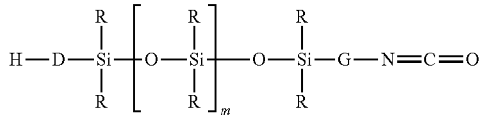

wherein D is an alkyl radical having 1 to 6 carbon atoms,

G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (c) a diisocyanate, wherein total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III):

(III)

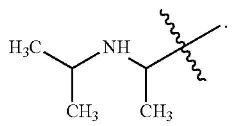

In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV):

(IV)

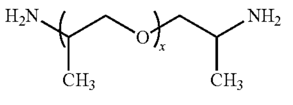

wherein x is an integer in the range of 2 to 70; or a poly(ethylene glycol) diamine having a formula (V):

(V)

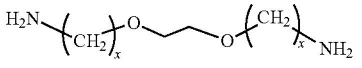

wherein x is 2 or 3.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including JEFFAMINE® D, ED, EDR and SD series.

In some aspects, silicone polyurea copolymers synthesized in accordance with inventive principles are soluble in water, alcohol (e.g., isopropanol), alcohol-water mixtures, and buffer solutions. These silicone polyurea copolymer compositions can preferentially bind to surfaces out of solution and provide a passivated surface. Not to be bound to theory, this may be due to a surfactant effect, the urea linkages, and/or the silicone block within the copolymer.

Optionally, biomolecules can be included in the silicone polyurea block copolymer coatings described herein. Passivation provided by inventive silicone polyurea block copolymers can complement a biomolecule surface, as the polyurea copolymers can decrease denaturation of proteins during use of the surface for in vitro assays or in vivo. The silicone polyurea copolymer can be provided in solution in water, alcohol, an alcohol-water mixture, or a buffer solution.

Thus, in some aspects, inventive concepts provide a composition comprising:

(a) a solvent selected from water, alcohol, an alcohol-water mixture, or a buffer; and (b) a silicone polyurea copolymer in solution, the silicone polyurea copolymer comprising a reaction product of:

(i) a diamine composition comprising a poly(ethylene glycol) diamine having a formula (I), (II), or a combination of diamines of formulae (I) and (II):

(I)

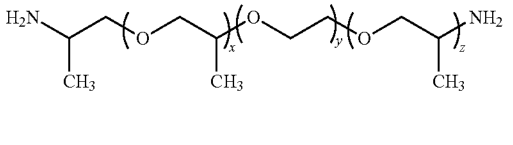

wherein y is an integer in the range of 2 to 40, and x+z is an integer in the range of 1 to 8; and (II)

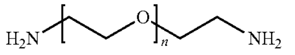

wherein n is an integer in the range of 1 to 500;

(ii) a monofunctional silicone isocyanate having a formula:

(VIII)

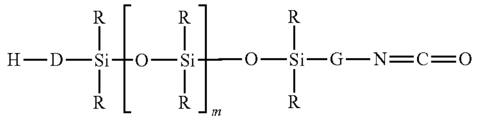

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (c) a diisocyanate, wherein the total isocyanate is present in a molar ratio with total diamines in (a) in a range of 1.5:1 to 1.05:1. In some implementations, total isocyanate is present in molar ratio with total diamines in (a) in a range of 1:1.05 to 1:1, or in a range of 1.3:1 to 1.2:1, or in a range of 1:1.2 to 1:1.3.

In some implementations, the diamine composition of (a) comprises a secondary amine version of the poly(ethylene glycol) diamine represented by formula (III). In some implementations, the diamine composition of (a) comprises a poly(propylene glycol) diamine having a formula (IV); or a poly(ethylene glycol) diamine having a formula (V), as represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including JEFFAMINE® D, ED, EDR and SD series.

Illustrative solvents include those listed as reaction solvents (THF, ethyl acetate, ether, dimethyl sulfoxide (DMSO), dimethylformamide (DMF), acetone, methyl ethyl ketone, chloroform, dichloromethane), as well as water, alcohol, water-alcohol mixtures, buffers, and other commonly used solvents. In some implementations, preferable solvents for the silicone polyurea copolymer include alcohol, water, aqueous buffers and mixtures thereof.

As used herein, a "solution" refers to a homogeneous mixture composed of two or more substances, i.e., a solute dissolved in a solvent. Correspondingly, when a solute is dissolved in a solvent, it is referred to as "in solution." The term "aqueous solution" refers to any solution containing a solute dissolved in water. The term "buffer solution" is used in its common manner to include aqueous solutions consisting of a mixture of a weak acid and its conjugate base, or vice versa, wherein the solution resists change in pH when acid or alkali is added to it.

In some implementations, silicone polyurea block copolymers can be provided in solution, with a total solids content of 10% or lower, or 5% or lower, or 4% or lower, or 3% or lower, or 2% or lower, or 1% or lower. It will be appreciated that the solids content of the solution can be selected depending upon final use of the silicone polyurea block copolymer solution.

Solubility refers to the property of the copolymer to dissolve in a solvent of choice. Slightly soluble means that about 100 to 1000 parts solvent, for example, are needed to dissolve 1 part solute, while "sparingly soluble" means that about 30 to 100 parts solvent, for example, are needed to dissolve 1 part solute. Soluble means that about 10 to 30 parts solvent, for example, are needed to dissolve 1 part solute. Freely soluble means that about 1 to 10 parts solvent, for example, are needed to dissolve 1 part solute. Very soluble (also referred to herein as "highly soluble") means that less than 1 part solvent is needed to dissolve 1 part solute.

Conversely, "insoluble" means that a copolymer is unable to dissolve in a solvent of choice, such as water, an alcohol, or an alcohol-water mixture.

Advantageously, silicone polyurea block copolymer compositions in accordance with inventive principles can provide durable coatings on surfaces. In some aspects, the adherence of a coating comprising inventive silicone polyurea copolymer compositions is sufficient to withstand not only washing, but also contact of surfaces during use, for example, microsphere-microsphere contact upon magnetic separation.

Silicone polyurea block copolymers form coatings on many substrates. These coatings are generally films when more than a few monolayers are present (as in physisorption). The films themselves may be characterized either on a surface or as an isolated material by casting a silicone polyurea block copolymer coating solution, removing solvent by drying, and peeling up the resulting material. The material properties vary depending upon the molecular weight of the silicone polyurea block copolymer and presence of crosslinking due to branching or latent reactive groups.

In some aspects, inventive silicone polyurea block copolymers are generally lower molecular weight (e.g., Mw 100,000 or less) and linear/unbranched. These silicone polyurea block copolymers are softer than many polyureas, with a Shore D Hardness Value of 30 D or less, or 25 D or less, or 20 D or less, or 10 D or less.

In some implementations, inventive polyurea copolymers provide smooth, non-tacky coatings when applied to substrate surfaces. Smooth, non-tacky surfaces can be desirable for many industrial applications. In some aspects, inventive silicone polyurea copolymers can exhibit a Young's modulus that is higher than known silicone polyureas, for example greater than 400 psi (2,758,000 Pa), or greater than 450 psi. This modulus is greater than the Dahlquist criteria of 10,000 Pa used to define pressure sensitive adhesives.

In some implementations, silicone polyurea copolymer coatings can vary in thickness from a physisorbed monolayer of less than 10 nm to cast films that are greater than 1 mm in thickness. In some implementations, the coating thickness is 10 microns or less, or 5 microns or less, or 2 microns or less.

Additional advantages can be seen in the durability of coatings comprising inventive silicone polyurea copolymer compositions. In some aspects, silicone polyurea copolymer coated polystyrene plates are suitable for extended wash, incubation, and agitation steps. In addition, inventive silicone polyurea copolymer coating compositions can bind to a large variety of substrate materials.

The stable binding of the silicone polyurea copolymer to substrate is also surprising due to the lack of covalent bonding or heating step to induce polymer chain entanglement. Most PEG-based coatings require covalent bonding or they will be removed by rinsing, proteins or surfactant treatments. Optional components, such as latent reactive groups, can further enhance binding of the silicone polyurea block copolymer to substrate. However, it is understood such latent reactive groups are not required. Inventive coating processes are quite simple, the substrate to be coated is incubated in aqueous silicone polyurea copolymer solution at room temperature, then rinsed with water. A curing step is not required; the coated substrate can be left to dry at room temperature in air. An inert atmosphere is not required. The silicone polyurea copolymer can also be applied by spray, dip, or other coating method known to a person with skill in the art.

The resulting silicone polyurea copolymer coated substrates have reduced adhesion of biomolecules including proteins, cells, tissue, bacteria, biofilm, and others. Examples show that microspheres coated with the silicone polyurea copolymer have similar or improved passivation to that of bovine serum albumin (BSA) the gold standard of blockers for diagnostic assays such as ELISA, western blot, etc. In theory, this may be due to the polyethylene glycol (PEG) content of the silicone polyurea copolymers; however, the magnitude of the passivation effect is much larger than typical PEG coatings. The urea linkage may also contribute to passivation due to hydrogen bonding or a chaotropic effect. The silicone polyurea copolymer coating compared to a typical PEG-based coating is both better performing and more easily applied.

As used herein, "passivation" is the process of making a surface "passive," that is, a surface film or coating is created that results in a reduction of biological responses when exposed to biological fluids (for example, reduction of cellular attachment and proliferation, protein adsorption or reduction of cellular responses mediating inflammation). A passivating coating forms a surface having improved biological passivation as compared to the uncoated material, when exposed to conditions of use (for example, in a human body). Biological fluids (or "biofluids") can include intracellular fluid and extracellular fluid (intravascular, interstitial, lymphatic, transcellular), such as blood, saliva, urine, cerebrospinal fluid, blood plasma, ocular fluids (aqueous humour and vitreous humour), bile, lymph (endolymph and perilymph), exudates, gastric fluids (gastric acid, gastric juice), mucus, pericardial fluid, peritoneal fluid, pleural fluid, pus, rheum, sebum, serous fluid, semen, serum, amniotic fluid and cerumen.

In some implementations, coatings comprising inventive silicone polyurea copolymers can provide lubricious surfaces. Lubricity, as measured by a reduction of friction force as two surface rub against one another, is very important in many devices to reduce wear and improve efficient function. Lubricity can be improved by adding an external lubricant such as water, silicone oil, graphite or Teflon particles or other means. However, an external lubricant will dissipate over time and can create contaminants for other parts of a device. The coatings described herein can be used to improve lubricity in the dry state, without addition of an external lubricant. The coated piece provides a surface with reduced friction against another contacting surface and is durable to wear. The other contacting surface can be the same material or a different material altogether. Since the coating is firmly adhered to the substrate, there is no loss of lubricity or contamination of other portions of the device. The silicone triblock urea copolymer is designed so that urea portion will adhere to the substrate and the silicone portion will provide lubricity, much like silicone oil does. Being on the termini, the silicone blocks are sufficiently large and free to move while being tethered to the surface by the urea block and may behave "liquid-like" to aid lubrication. Coatings applied to a surface and dried in air will increase the likelihood of a silicone block at the air-coating interface due to air and silicone's hydrophobicity.

In some implementations, inventive silicone polyurea copolymers provide improved dry lubricity by reducing frictional resistance of the coated surface against another surface. In some embodiments, silicone polyurea copolymer coatings can reduce frictional resistance by at least 50% against another (e.g., uncoated) substrate, or by at least 60%, or by at least 70%, or by at least 75% against another substrate. For example, if the coefficient of friction of a surface (uncoated) is 1.00, a surface coated with silicone polyurea copolymer that reduces the frictional resistance by 75% would have a new coefficient of friction of 0.25. An illustration of this effect is shown in the Examples.

Similar concepts apply to surfaces that are maintained in an aqueous or humid environment for long periods of time. Such surfaces can be rendered "passive" via the silicone polyurea block copolymer compositions described herein, such passivity being observed as reduced binding of unwanted materials (biological or chemical) to the surface. For example, inventive silicone polyurea block copolymers can be provided on a surface maintained in an aqueous environment to reduce formation of biofilms or other unwanted materials on the surface.

As used herein, the term "durability" refers to the wear resistance of a coating, or the ability of the inventive copolymer coatings to be maintained on a substrate surface when subjected to forces or conditions typically encountered during use (for example, normal force, shear force, and the like). A more durable coating is less easily removed from a substrate by abrasion. For applications involving long-term exposure to aqueous environments (such as water treatment vessels and/or lines), durability can refer to the ability of the coating to maintain a passivating surface on the application surface. Passivation properties can be measured using common techniques, based upon the application. Durability of a coating can be assessed by subjecting a substrate (such as a medical device) to conditions that simulate use conditions as is demonstrated in the Examples.

Inventive silicone polyurea copolymers comprise a reaction product of: (a) a diamine composition comprising a polyethylene glycol diamine; (b) a monofunctional silicone isocyanate; and (c) a diisocyanate.

Suitable polyethylene glycol diamines can have a formula (I) or (II):

(I)

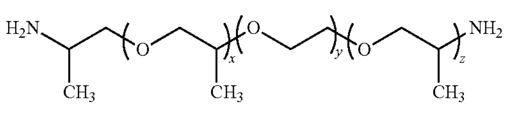

wherein y is an integer in the range of 2 to 40, and x+z is an integer in the range of 1 to 8; or (II)

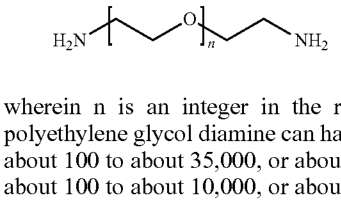

wherein n is an integer in the range of 1 to 500. The polyethylene glycol diamine can have a molecular weight of about 100 to about 35,000, or about 100 to about 25,000, or about 100 to about 10,000, or about 500 to about 25,000, or about 500 to about 10,000, or about 500 to about 5,000. In some implementations, the diamine composition includes a combination of polyethylene glycols of formula (I) and formula (II).

In some implementations, the diamine composition of (a) comprises a secondary amine version of the poly(ethylene glycol) diamine represented by formula (III). In some implementations, the diamine composition of (a) comprises a poly(propylene glycol) diamine having a formula (IV); or a poly(ethylene glycol) diamine having a formula (V), as represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including JEFFAMINE® D, ED, EDR and SD series.

Optionally, the diamine composition can further comprise a dipiperidyl alkane. In some aspects, the dipiperidyl alkane has a formula:

(VI)

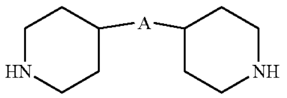

where A is a C0 to C 8 bivalent alkyl radical. Illustrative dipiperidyl alkanes include dipiperidyl propane, dipiperidyl methane, dipiperidyl ethane, dipiperidyl butane, dipiperidyl pentane, dipiperidyl hexane, dipiperidyl heptane, and dipiperidyl octane, and bipiperidine.

In accordance with inventive concepts, when the dipiperidyl alkane is present, the diamine composition can comprise 20 to 99.9 molar percent of the polyethylene glycol and 0.1 to 80 molar percent of the dipiperidyl alkane.

As used herein, "alkyl" (by itself or as part of another substituent) refers to a saturated or unsaturated branched, straight-chain or cyclic monovalent hydrocarbon radical having the stated number of carbon atoms (for example, C1-C6 means one to six carbon atoms) that is derived by the removal of one hydrogen atom from a single carbon atom of a parent alkane, alkene or alkyne. Illustrative alkyl groups include, but are not limited to, methyl, ethyls (such as ethanyl, ethenyl, ethynyl), propyls, butyls, phenyls, and the like. It will be understood that "bivalent" alkyl radicals are derived from removal of two hydrogen atoms from a parent alkane, alkene or alkyne.

Surprisingly, it was found that several diamines produced copolymers that were completely insoluble in isopropanol and water. These diamines are thus less desirable for use in connection with inventive silicone polyurea copolymers, since water and/or alcohol solubility is a significant advantage. As shown in the Examples, 1,3-diaminopropane, 1,3 diamino-2-propanol, cadaverine, lysine, and m-xylylenediamine produced copolymers that were completely insoluble. In some aspects, inventive silicone polyurea copolymers are produced utilizing diamines compositions that do not comprise 1,3-diaminopropane, 1,3 diamino-2-propanol, cadaverine, lysine, and m-xylylenediamine. In some aspects, copolymers that do not include secondary alcohol functional groups can be advantageous. Thus, in some implementations, inventive copolymers do not include secondary alcohol functional groups.

In accordance with inventive concepts, silicone polyurea block copolymers are formed using a monofunctional silicone isocyanate having a formula:

(VIII)

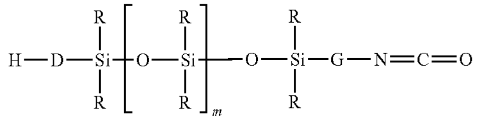

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300.

The diisocyanate used to prepare inventive silicone polyurea copolymer compositions can have a formula:

$$OCN—B—NCO \qquad (VII)$$

where B is a bivalent alkyl radical having 2 to 20 carbon atoms.

Illustrative diisocyanates include hexane diisocyanate, isophorone diisocyanate, naphthalene diisocyanate, toluene-2,4-diisocyanate, methylenediphenyldiisocyanate, p-phenylenediisocyanate, meta-trimethylxylylenediisocyanate, methylene-bis(4-cyclohexylisocyanate), and hydrogenated methylenediphenyldiisocyanate.

In some aspects, the total isocyanate (including monofunctional silicone isocyanate and diisocyanate) can be present in a molar ratio with total diamines in a range of 1.5:1 to 1.05:1, or in a range of 1:1.05 to 1:1.5 can be preferred, and a ratio in a range of 1.3:1 to 1.2:1, or 1:1.2 to 1:1.3 can be particularly preferred.

In some implementations, the relatively low molecular weight and bivalent character of monomeric units (diamines and diisocyanates) can provide silicone polyurea block copolymers having a relatively lower molecular weight. This, in turn, can provide desirable solubility in aqueous solvent systems.

Methods of making silicone polyurea copolymers are also provided. Inventive methods comprise polymerizing under reactive conditions:

(1) a diamine composition comprising a polyethylene glycol diamine having Formula (I) or (II) above, and, optionally, a dipiperidyl alkane;

(2) monofunctional silicone isocyanate having formula (IV) above; and (3) diisocyanate having a formula (V) above.

In some implementations, the diamine composition of (a) comprises a secondary amine version of the poly(ethylene glycol) diamine represented by formula (III). In some implementations, the diamine composition of (a) comprises a poly(propylene glycol) diamine having a formula (IV); or a poly(ethylene glycol) diamine having a formula (V), as represented above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Texas, USA), under the JEFFAMINE® product lines, including JEFFAMINE® D, ED, EDR and SD series.

Advantageously, the reaction can be performed under relatively simple conditions, including mild solvents. A condensation reaction can proceed at room temperature with stirring.

The resulting silicone polyurea is a triblock copolymer with repeating diamine and diisocyanate units, and silicone terminal segments. Illustrative silicone polyurea copolymers are provided in the Examples. In some aspects, the silicone polyurea copolymer can comprise polyethylene glycol in amount in a range of 20 to 95, or 25 to 95 weight percent.

In some embodiments, additional molecular groups can be included in the polyurea block of the silicone polyurea copolymer. These groups can be part of the polyurea backbone introduced by copolymerizing a diamine or diisocyanate with the desired molecular group, or these groups can be pendant to the polyurea backbone when a diamine or diisocyanate has a pendant group that contains the desired molecular group. A pendant group could be introduced for instance by polymerizing a diamine with a pendant group that is not reactive with diisocyanate but can be functionalized after the silicone polyurea is formed. For example, a diamine with a pendant t-butyl ester can be introduced into the polyurea backbone. In this aspect, these t-butyl esters are stable to amines and the polymerization conditions, but can be converted to acids with mild acid hydrolysis. The subsequent pendant acid on the formed silicone polyurea could be used to covalently attach a variety of molecules through carbodiimide coupling or other methods known to those skilled in the art. Alternately, a diamine with the desired pendant group already in place could be used if it was not reactive to the amines, isocyanates or polymerization conditions. These additional functional groups included in the polyurea backbone or pendant from the polyurea backbone can include latent reactive groups, biomolecule groups, antimicrobial groups, or other desired functionalities. In these implementations, such additional components do not introduce branching or crosslinking of the polymer prior to coating application, but rather are used after a coating composition has been applied to a surface, to couple additional materials to the coated surface.

In some embodiments, a mono-amine or mono-isocyanate monomer other than silicone may be introduced on the second terminus of the silicone polyurea. In these implementations, the mono-functionalized monomer terminates the polymerization in the same manner as the silicone mono-isocyanate. Taking mono-aminobenzophenone as one example, the resulting polymerization product would be a statistical distribution of di-silicone terminated polyurea, mono-silicone, mono-benzophenone polyurea, and di-benzophenone polyurea. The silicone polyureas could be separated from the di-benzophenone polyureas by precipitation or other methods known to those skilled in the art. The mono-benzophenone monomer could be used to include latent reactive groups, biomolecule groups, antimicrobial groups, or other desired functionalities one terminus of the silicone polyurea copolymer. In these aspects, the silicone polyurea copolymer can have a modified block structure represented as A-B-F, with A being a silicone segment linked to the B segment through a urea linkage. The B segment is comprised of a random copolymer block of C-D repeating monomers linked through a urea group, where C is a hydrocarbon having 2 to 20 carbon atoms, and D is a polyethylene glycol/polypropylene glycol copolymer or dipiperidyl propane. In these embodiments, the F segment comprising a functional segment (such as latent reactive group, biomolecule group, antimicrobial group) linked to the B segment through a urea linkage. In these aspects, the F segment is a non-silicone segment. One skilled in the art would readily appreciate the variety of mono-amine or mono-isocyanate monomers that can be utilized in accordance with these aspects of the invention.

Latent reactive groups can include photoreactive groups, thermally reactive groups and/or chemically reactive groups. These groups can be considered to be "latent" in that they remain stable and nonreactive during conditions of storage and can become chemically reactive when exposed to reaction conditions (such as an energy source, chemical composition, or other).

"Photoreactive groups" or "photo-activatable reactive chemical groups" are chemically inert compounds that become reactive when exposed to actinic energy. Typically, groups are chosen that can be activated using either ultraviolet or visible light. When exposed to an appropriate energy source, a photoreactive species undergoes a transformation from an inactive state (ground state) to a reactive intermediate capable of forming covalent bonds with appropriate materials. Useful photoreactive groups are described, for example, in U.S. Pat. No. 5,002,582 (Guire et al.) and U.S. Pat. No. 7,772,393 B2 (Guire et al.).

Illustrative photoreactive groups include, but are not limited to, aryl ketones, azides, diazos, diazirines, ketones, and quinones. The photoreactive groups generate active species such as free radicals including, for example, nitrenes, carbenes, and excited states of ketones upon absorption of electromagnetic energy.

In some implementations, the photoreactive group can be an aryl ketone, such as acetophenone, benzophenone, anthrone, and anthrone-like heterocycles (heterocyclic analogs of anthrone such as those having N, O, or S in the 10-position), or their substituted (for example, ring-substituted) derivatives. Examples of aryl ketones include heterocyclic derivatives of anthrone, including acridone, xanthone, and thioxanthone, and their ring-substituted derivatives. Other suitable photoreactive groups include quinones such as, for example, anthraquinone.

Illustrative azides include arylazides such as phenyl azide and 4-fluoro-3-nitrophenyl azide; acyl azides ($—CO—N_3$) such as benzoyl azide and p-methylbenzoyl azide; azido formates ($—O—CO—N_3$) such as ethyl azidoformate and phenyl azidoformate; sulfonyl azides ($—SO_2—N_3$) such as benzenesulfonyl azide; and phosphoryl azides $(RO)_2PON_3$ such as diphenyl phosphoryl azide and diethyl phosphoryl azide.

Illustrative diazo compounds include diazoalkanes ($—CHN_2$) such as diazomethane and diphenyldiazomethane; diazoketones ($—CO—CHN_2$) such as diazoacetophenone and 1-trifluoromethyl-1-diazo-2-pentanone; diazoacetates ($—O—CO—CHN_2$) such as t-butyl diazoacetate and phenyl diazoacetate; and beta-keto-alpha-diazoacetates ($—CO—CN_2—CO—O—$) such as t-butyl alpha diazoacetoacetate. Diazo compounds are also thermally reactive groups.

Other photoreactive groups include diazirines ($—CHN_2$) such as 3-trifluoromethyl-3-phenyldiazirine, and ketenes ($CH{=}C{=}O$) such as ketene and diphenylketene.

Photoreactive groups can be non-ionic or ionic. Illustrative non-ionic photoreactive groups include the tetrakis (4-benzoylbenzyl ether) or the tetrakis (4-benzoylbenzyl ester) of pentaerythritol. Illustrative ionic photoreactive groups are discussed in US 2012/0258313 A1 (Wen et al.), U.S. Pat. No. 6,278,018 (Swan) and U.S. Pat. No. 5,714,360 (Swan et al).

In some implementations, latent reactive group(s) can comprise one or more thermally reactive groups. Thermal activation may be advantageous when exposure to UV light is not practical (for example for the inner lumen of a tubular medical article) or is undesirable (for example when coating materials contain UV light-sensitive components). Thermally reactive groups can also be advantageous in coatings exhibiting low transmission of UV light. Suitable external energy sources for these groups include heat sources.

Thermally reactive groups can include pairs of atoms having a heat sensitive (labile) bond between the atoms. Examples of such pairs of atoms include oxygen-oxygen (per-esters and peroxides), nitrogen-oxygen, and nitrogen-nitrogen. Examples of thermally reactive groups useful in present embodiments include 4,4' azobis(4-cyanopentanoic acid) and analogs of benzoyl peroxide. External energy sources to produce thermal energy can be used to activate a thermally reactive group.

In some embodiments, the latent reactive group can include one or more nitrenogenic groups. For example, a latent reactive group can comprise a perhalophenylazide (PHPA), such as perfluorophenylazide (PFPA). Perfluorophenylazides typically can be derived from 4-azido-2,3,5,6-tetrafluorobenzoic acid. A "nitrenogenic group" is a chemical moiety that becomes a nitrene group when exposed to a reaction-energy source. An azido group is an example of a nitrenogenic group. In turn, a "nitrene group" (also generally termed "nitrene" or "nitrene intermediate") is a particular form of nitrogen group regarded as the nitrogen analog of carbenes. Like carbenes, nitrenes are generally regarded as intermediates that are highly reactive and may not be isolatable under ordinary conditions. Important nitrene reactions include, but are not limited to, addition or insertion in C—H, N—H, O—H, and C—C bonds (single and double).

In some implementations, the latent reactive groups can comprise chemical reactive groups. Suitable chemical reactive groups can be referred to as redox initiators, redox catalysis agents, or redox activation agents. In general, combinations of organic and inorganic oxidizers, and organic and inorganic reducing agents are used to generate radicals for polymerization. A description of redox initiation can be found in *Principles of Polymerization,* 2$^{nd}$ Edition, Odian G., John Wiley and Sons, pages 201-204 (1981), that part of which is herein incorporated by reference. In some implementations, the chemical reactive group can comprise a catechol-based group, such as catecholamine (that is, dopamine, or 4-(2-aminoethyl)benzene-1,2-diol), and such groups can be activated with oxidizing agents.

In some implementations, silicone polyurea block copolymers can include one or more biomolecules or dyes. In accordance with inventive principles, biomolecules can be selected to provide additional features to the copolymer, such as binding sites for additional components (thus creating customizable copolymers), antimicrobial properties, passivating properties, activation of enzymes, conjugation of antibodies, and the like.

Illustrative biomolecules include saccharides (mono- and polysaccharides), proteins, nucleic acids, and the like. Illustrative saccharides include hyaluronic acid, heparin, glycosaminoglycans, chitosan, glucosamines, and the like. Illustrative proteins include avidin (including streptavidin); antibodies; albumin, globulin, fibrinogen, and other blood proteins; enzymes; collagen, fibronectin, elastin, laminin, and other extracellular matrix proteins.

When included, dyes can be selected to provide suitable visualization tools for the desired application. Illustrative dyes include fluorescent dyes such as green fluorescent protein (GFP), fluorescein isothiocyanate (FITC), coumarin, Alexa Fluor, Cy3, Cy5, Oregon Green, Pacific Blue, Pacific Green, Pacific Orange, tetramethylrhodamine (TRITC), Texas Red, and the like.

In accordance with inventive concepts, silicone polyurea block copolymers can be prepared to include latent reactive groups, biomolecules, dyes, or a combination of any two or more of these.

When di-amine latent reactive groups are combined with inventive diamine compositions comprising a polyethylene glycol diamine, monofunctional silicone isocyanate, and diisocyanate in reaction solvent (e.g., alcohol), resulting silicone polyurea block copolymers can include the latent reactive groups incorporated within the copolymer backbone, or pendant to the copolymer backbone (i.e., at the end-groups). It is understood that mono-amine compounds would provide end-group coupling, while diamine compounds could be incorporated into the copolymer backbone and/or at copolymer chain end-groups.

In accordance with inventive principles, latent reactive groups (such as photoreactive groups) can be chosen that do not adversely affect solubility of the silicone polyurea block copolymers. Such latent reactive groups can themselves be soluble in water, alcohol, alcohol-water, or buffer solutions. Alternatively, less soluble latent reactive groups can be added in molar amounts that do not affect the overall solubility of the silicone polyurea copolymer.

Some illustrative reaction conditions are provided in the Examples.

Silicone polyurea copolymers produced in accordance with inventive principles can be used as coating compositions for a wide variety of surfaces. In some aspects, such coating compositions can be particularly useful when utilized in connection with surfaces that contact biological fluids. The surface can be a surface of an implantable medical device, a medical device for temporary insertion into a patient's body, devices that contact biological fluids outside a patient's body (such as tubing or the like), or an in vitro diagnostic device. Inventive silicone polyurea copolymer compositions can also be applied to substrates outside the implantable medical device field, as will be apparent from the variety of materials that can be coated with the inventive silicone polyurea copolymers. Illustrative classes of substrates outside the medical device field include water treatment system components (vessels, tanks, containers, filters, membranes, pipes, and the like), condenser coils, and/or marine vessels (such as boat or ship hulls, tanks, docks and the like), and marine vessel components (such as motors, anchors, rudders, and the like).

The particular form of the substrate is not critical. In accordance with inventive aspects, the substrates can be provided in a number of different formats. Illustrative substrates include, for example, solid tangible surfaces and particles.

Suitable materials for fabrication of solid tangible surfaces include materials commonly used to fabricate implantable medical devices. The solid tangible surface is optionally intended to function in contact with tissue and/or fluids of the body. Examples of suitable support materials include those materials commonly used to fabricate implantable medical devices such as metals, minerals or ceramics, fabric, carbon-based materials (e.g., biomaterial), and polymers.

Suitable metals include, for example, aluminum, chromium, cobalt, iron, tantalum, titanium, and alloys thereof, as well as nitinol and other nickel-titanium alloys, and stainless steels. Examples of suitable minerals or ceramics include alumina, hydroxyapatite, quartz, sapphire, silica and glasses. Illustrative carbon-based materials include pyrolytic carbon, as well as carbon materials obtained by thermal degradation (thermolysis, pyrolysis) or organic compounds, as well as materials obtained by physical vapor deposition (PVD) techniques.

In some aspects, the silicone polyurea copolymers can be useful in connection with substrates fabricated of a synthetic or natural polymer. For example, the substrate can be fabricated from synthetic polymer such as Parylene™ (tradename for a variety of chemical vapor deposited poly (p-xylylene) polymers), polyamides (such as polyether block amides such as PEBAX™), polyesters, polyethylenes, polyethylene terephthalates (PET), poly(meth)acrylates, polyacetates, polyvinylacetates, sulfonic acid-substituted polymers, polyacrylamide polyethylene glycols, polyethyleneimines, polylactic acids, polyglycolic acids, polylactide-co-glycolides, polyvinyl alcohols, polyvinyl pyrrolidones, quaternary amine-substituted polymers, conductive polymers (for example, polyvinylpyridine, polyacetylenes, polypyrroles), poly-(p-pheyleneterephthalamides), polyphosphazenes, polypropylenes, polyetetrafluoroethylenes, polysiloxanes, inorganic synthetic elastomers, organic polymers, or copolymers thereof or combinations of any of these. In other embodiments, the substrate can be formed from natural polymers such as polysaccharides, proteins, nucleic acids or organic polymers.

In some aspects, a suitable substrate can be fabricated of a polymeric material. Exemplary polymers include silicones, polyolefins, vinyl polymers, polystyrenes, polyacrylates (including polymethacrylate), poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose-based plastics, and rubber-like plastics, providing surfaces that can be modified as described herein. See generally, "Plastics", pp. 462-464, in Concise Encyclopedia of Polymer Science and Engineering, Kroschwitz, ed., John Wiley and Sons, 1990. Illustrative polyolefins include polyethylene, such as high density polyethylene (HDPE), polytetrafluoroethylene, and the like, as well as polypropylene and the like.

In some implementations, polyurea copolymers are provided as coatings in implantable medical devices. Illustrative implantable medical devices include, but are not limited to, vascular devices such as guidewires, stents, stent grafts, covered stents, catheters (single use and long-term), valves, distal protection devices, aneurysm occlusion devices, septal defect closures; cardiac devices such as artificial hearts and heart assist devices such as defibrillators, pacemakers and pacing leads; orthopedic devices such as joint implants and fracture repair devices; dental devices such as dental implants and repair devices; ocular devices and glaucoma drain shunts; urological devices such as penile, sphincter, urethral, bladder and renal devices; neurological devices such as neurostimulators, drainage catheters, shunts, fixation devices, coils (e.g., embolization), electrodes, myeloscopes, guidewires, stents, grafts, probes, meshes, and matrices; synthetic prostheses such as breast prostheses and artificial organs; surgical closures; laparoscopic fixation devices; endosurgical components; tracheal, esophageal or bronchial tubes; ear tube components; fixation devices (plates, screws, tacks, pins, nails); shunts; dialysis components; filters; ports; sensors; scaffolds; patches; and the like. In some implementations, the medical article is a catheter, such as a silicone catheter.

Non-implanted medical articles can be provided with inventive coatings as well, including such articles as transdermal drug delivery devices (such as patches, bandages, dressings, and the like); dialysis devices and associated tubing, catheters, membranes and grafts; autotransfusion devices; vascular and surgical devices including a wide variety of catheters (atherectomy, angiographic, clot extraction, angioplasty, electrophysiology, and the like), intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, breathing circuit connectors, stylets (vascular and non-vascular), guidewires (coronary, peripheral, and the like); dialators (e.g., urinary, etc.); surgical instruments (e.g., scalpels and the like); endoscopic devices (such as endoscopic surgical tissue extractors, esophageal stethoscopes); hearing aids; and general medical and medically related devices including blood storage bags, umbilical tape, membranes, wound dressings (including bandages), wound management devices, needles, percutaneous closure devices, transducer protectors, uterine bleeding patches, clamps, cannulae; as well as diagnostic slides (such as oligonucleotide arrays, microarrays, protein chips and fluorescence in situ hybridization (FISH) slides); chromatographic support materials; cell culture devices; biosensors; and the like.

Non-implanted medical devices include, but are not limited to, diagnostic slides such as gene chips, DNA chip arrays, microarrays, protein chips, and fluorescence in situ hybridization (FISH) slides; arrays including cDNA arrays, and oligonucleotide arrays; chromatographic support materials, cell culture devices, biosensors, microfluidic devices, and the like.

Generally speaking, in vitro diagnostics (IVD) are considered medical devices. In accordance with inventive concepts, medical diagnostics include articles used in vitro for the examination of specimens such as blood, urine or tissue with the goal of obtaining a diagnosis from assays in a controlled environment outside a living organism. Medical diagnostics can include laboratory consumables (plates, tubes, trays, capillaries, containers, and the like), cell culture ware, slides, assays, microarrays, sensors, and the like.

In some implementations, inventive silicone polyurea copolymers can be used to passivate the surface of microparticles, such as magnetic microparticles. Illustrative particles include micro- and nanoparticles including but not limited to magnetic particles, polystyrene particles, metallic particles. Additional devices include microwell and larger plates; slides; membranes; tubing; gels; petri dishes; cell cultureware including but not limited to flasks, plates, tubes, and vials; bioreactors; aquatic or marine vessels and structures and other surfaces subject to biofouling; catheters; guidewires; introducers; sensor surfaces; and other medical device surfaces.

In further aspects, inventive concepts provide a medical device having a surface containing a passivating coating, the passivating coating comprising a silicone polyurea copolymer comprising a reaction product of: (a) a diamine composition comprising a polyethylene glycol diamine having a formula (I), (II), or a mixture of (I) and (II); (b) monofunctional silicone isocyanate; and (c) a diisocyanate. Components (a), (b) and (c) are as described herein.

Inventive concepts also provide methods for forming a passivating coating or a lubricious coating on a surface of a medical device comprising steps of:

(a) Providing a silicone polyurea copolymer solution comprising a reaction product of (i) a diamine composition comprising a polyethylene glycol diamine having a formula (I), (II), or a mixture of (I) and (II); (ii) a monofunctional silicone isocyanate having a formula (VIII); and (iii) diisocyanate, the reaction product being provided in water, an alcohol, or an alcohol-water mixture;
(b) Covering the surface of the medical device with the silicone polyurea copolymer solution; and
(c) Removing the silicone polyurea copolymer solution from the surface.

The silicone polyurea copolymer solution can be provided onto the surface by any suitable method, including spray coating, immersion, spreading the solution onto the surface, and the like. The silicone polyurea copolymer solution can be removed from the surface by any suitable method, such as rinsing with a solution that is the same as the solvent for the silicone polyurea copolymer solution (e.g., water, alcohol, or an alcohol-water mixture). Advantageously, some embodiments of the inventive methods do not include a curing step, such as by UV illumination, heating to a desired temperature, or the like.

In some implementations, inventive silicone polyurea block copolymers adhere to a surface through adsorption, more specifically, physisorption. As contemplated herein, physisorption involves adsorption in which the forces involved are intermolecular forces (van der Waals forces), and which do not involve a significant change in the electronic orbital patters of the species involved. In the case of physisorption, the adsorbed species (coated silicone polyurea block copolymers) are chemically identical with those in the fluid phase, so that the chemical nature of the fluid is not altered by adsorption and subsequent desorption. Equilibrium is established between the adsorbate and the fluid phase. In some aspects, physisorption can take place in water, alcohol, alcohol-water mixtures or buffers. Association of silicone polyurea block copolymers via physisorption can have significant advantages, since the silicone polyurea copolymers associate with a surface without drying. Thus, the ability to coat silicone polyurea block copolymers onto a surface via inventive concepts can provide more uniform coatings through this occurrence of physisorption. In some implementations, inventive silicone polyurea block copolymers can provide multiple coating layers on a surface. This is in contrast to chemisorption, where the adsorbed molecules are linked to the surface by valence bonds and thus typically occupy certain adsorption sites on the surface, resulting in only one layer of chemisorbed molecules (monolayer adsorption).

Surfaces can also be coated by dipcoating, casting, or spray coating. In these cases, the silicone polyurea block copolymer is formed prior to coating and applied as a single solution, in contrast to a two part pre-polymer spray polyurea application that undergoes chemical reaction upon combination in the spray. In accordance with inventive concepts, surfaces can be coated by simply dipping into the silicone polyurea block copolymer solution and air drying to remove the solvent. Illustrative solvents include alcohols, water, alcohol-water mixtures, and buffer solutions.

In some aspects, coating thickness and uniformity can be controlled by extraction rate and dwell time, and other techniques known to persons skilled in the art. The silicone polyurea block copolymer coating can be applied as one coated layer, or as several layers. The silicone polyurea block copolymer coating can be applied as a topcoat over a primer layer if desired, or as a primer layer to increase adhesion for a subsequent topcoat of either further polyureas or alternate non-polyurea coatings meant to improve the surface properties of the substrate.

Advantageously, the silicone polyurea block copolymer coatings do not require crosslinking to remain on the surface; however, crosslinking by latent reactive groups, such as photoactivable groups, can be used to increase durability to use conditions. For example, silicone polyurea block copolymers containing 4, 4'-diaminobenzophenone, can be photoactivated to form covalent bonds between the silicone polyurea copolymer and the substrate and/or between the silicone polyurea copolymers and/or between the silicone polyurea copolymer and other molecules that are desired on the surface. These new covalent bonds can connect a silicone polyurea copolymer coating to a substrate, increase durability of a silicone polyurea copolymer coating, or immobilize additional coating layers and/or coating components such as other non-polyurea polymers. Further illustration is provided in the examples. The latent reactive groups used in this manner are distinct from and do not include the diisocyanate/diamine chemistry used to crosslink other polyurea coatings.

The embodiments of the present invention described herein are not intended to be exhaustive or to limit the invention to the precise forms disclosed. Rather, the embodiments are chosen and described so that others skilled in the art can appreciate and understand the principles and practices of the present invention. This application is intended to cover adaptations or variations of the present subject matter.

All publications and patents mentioned herein are hereby incorporated by reference to the same extent as if each individual publication or patent application was specifically and individually indicated by reference. The publications and patents disclosed herein are provided solely for their disclosure. Nothing herein is to be construed as an admission that the inventors are not entitled to antedate any publication and/or patent. Including any publication and/or patent cited herein.

In the specification and in the claims, the terms "including" and "comprising" are open-ended terms and should be interpreted to mean "including, but not limited to . . . ". These terms are broader than, and therefore encompass, the more restrictive terms "consisting essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

EXAMPLES

Within the Examples, the monofunctional silicone isocyanate (PDMS, A-Bu, isocyanatopropyldimethylsilyl SC7115, MW~15,000) was obtained from Silar, Wilmington, NC.

Examples 1-7. Silicone Polyurea Copolymer Synthesis

Example 1

A silicone urea triblock copolymer was synthesized by combining 2.117 grams of Jeffamine ED1900 (1 mmole, Sigma Aldrich, Milwaukee, WI) and 0.20137 grams dipiperidyl propane (1 mmole, Sigma Aldrich, Milwaukee, WI) in 15 ml of isopropanol. To this, 0.300 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification.

Example 2

A silicone urea triblock copolymer was synthesized by dissolving 4.0394 grams of Jeffamine ED1900 (2 mmole, Sigma Aldrich, Milwaukee, WI) in 15 ml of isopropanol. To this, 0.0313 grams monofunctional silicone isocyanate (MW~15,000, 0.002 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification.

Example 3

A silicone urea triblock copolymer was synthesized by combining 0.41 ml of Jeffamine ED600 (0.7 mmole, Sigma Aldrich, Milwaukee, WI) and 0.273 grams dipiperidyl propane (1.3 mmole, Sigma Aldrich, Milwaukee, WI) in 15 ml of isopropanol. To this, 1.500 grams monofunctional silicone isocyanate (MW~15,000, 0.1 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification.

Example 4

A silicone urea triblock copolymer was synthesized by combining 2.0365 grams of Jeffamine ED1900 (1 mmole, Sigma Aldrich, Milwaukee, WI) and 0.2174 grams dipiperidyl propane (1 mmole, Sigma Aldrich, Milwaukee, WI) in 15 ml of isopropanol. To this, 0.0347 grams monofunctional silicone isocyanate (MW~15,000, 0.002 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product was soluble in isopropanol.

Example 5

A silicone urea triblock copolymer was synthesized by combining 0.23 ml of Jeffamine ED600 (0.4 mmole, Sigma Aldrich, Milwaukee, WI) and 0.3372 grams dipiperidyl propane (1.6 mmole, Sigma Aldrich, Milwaukee, WI) in 15 ml of isopropanol. To this, 0.31 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product was soluble in isopropanol.

Example 6

A silicone urea triblock copolymer was synthesized by combining 0.93 ml of Jeffamine ED600 (1.6 mmole, Sigma Aldrich, Milwaukee, WI) and 0.0842 grams dipiperidyl propane (0.4 mmole, Sigma Aldrich, Milwaukee, WI) in 15 ml of isopropanol. To this, 0.33 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product was soluble in isopropanol.

Example 7

A silicone urea triblock copolymer was synthesized by combining 0.3734 grams of Jeffamine ED600 (0.6 mmole, Sigma Aldrich, Milwaukee, WI) and 0.2955 grams dipiperidyl propane (1.4 mmole, Sigma Aldrich, Milwaukee, WI) in 15 ml of isopropanol. To this, 0.3007 grams monofunctional silicone isocyanate (MW~15,000, 0.02 mmoles, Silar, Wilmington, NC) was added with stirring for 15 minutes at room temperature, followed by the addition of 0.50 ml of isophorone diisocyanate (2.4 mmoles, Sigma Aldrich, Milwaukee, WI). The reaction mixture was stirred vigorously at room temperature for 1 hour, then used without further purification.

Examples 8-16. Silicone Polyurea Copolymer Synthesis, Insoluble

Example 8

A silicone urea triblock copolymer was synthesized by combining 0.13 ml of m-xylylene diamine (1.0 mmole, Sigma Aldrich, Milwaukee, WI) and 0.2145 grams dipiperidyl propane (1.0 mmole, Sigma Aldrich, Milwaukee, WI) in 15 ml of isopropanol. To this, 0.34 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product immediately precipitated and was insoluble in isopropanol.

Example 9

A silicone urea triblock copolymer was synthesized by combining 0.05 ml of m-xylylene diamine (0.4 mmole, Sigma Aldrich, Milwaukee, WI) and 0.96 ml of Jeffamine ED600 (1.6 mmole, Sigma Aldrich, Milwaukee, WI) in 15 ml of isopropanol. To this, 0.31 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product immediately precipitated and was insoluble in isopropanol.

Example 10

A silicone urea triblock copolymer was synthesized by combining 0.12 ml of cadaverine (1.0 mmole, Sigma Aldrich, Milwaukee, WI) and 0.6147 grams of Jeffamine ED600 (1.0 mmole, Sigma Aldrich, Milwaukee, WI) in 15 ml of isopropanol. To this, 0.3085 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product immediately precipitated and was insoluble in isopropanol.

Example 11

A silicone urea triblock copolymer was synthesized by combining 0.07 ml of 1,3-diaminopropane (1.0 mmole, Sigma Aldrich, Milwaukee, WI) and 0.6083 grams of Jeffamine ED600 (1.0 mmole, Sigma Aldrich, Milwaukee, WI) in 15 ml of isopropanol. To this, 0.3025 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product immediately precipitated and was insoluble in isopropanol.

Example 12

A silicone urea triblock copolymer was synthesized by combining 0.0936 grams of 1,3-diaminopropan-2-ol (1.0 mmole, Sigma Aldrich, Milwaukee, WI) and 0.58 ml of Jeffamine ED600 (1.0 mmole, Sigma Aldrich, Milwaukee, WI) in 15 ml of isopropanol. To this, 0.3092 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product immediately precipitated and was insoluble in isopropanol.

Example 13

A silicone urea triblock copolymer was synthesized by combining 0.0060 grams of L-lysine (0.04 mmole, Sigma Aldrich, Milwaukee, WI) and 1.9189 grams of Jeffamine ED1900 (0.96 mmole, Sigma Aldrich, Milwaukee, WI) and 0.2204 grams of dipiperidyl propane (1.0 mmole, Sigma Aldrich, Milwaukee, WI) in 7.5 ml of isopropanol with 7.5 ml of deionized water. To this, 0.0371 grams monofunctional silicone isocyanate (MW~15,000, 0.002 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour, then used without further purification. The resulting product immediately precipitated and was insoluble in isopropanol/water.

Example 14

A silicone urea triblock copolymer was synthesized by combining 0.421 grams dipiperidyl propane (2.0 mmole, Sigma Aldrich, Milwaukee, WI) and 0.3093 grams monofunctional silicone isocyanate (MW~15,000, 0.02 mmoles, Silar, Wilmington, NC) in 15 ml isopropanol with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour. The resulting product was insoluble in isopropanol and in water:isopropanol mixtures.

Example 15

A silicone urea triblock copolymer was synthesized by combining 0.3979 grams dipiperidyl propane (1.9 mmole, Sigma Aldrich, Milwaukee, WI) and 0.0.0687 grams of Jeffamine ED600 (0.1 mmole, Sigma Aldrich, Milwaukee, WI) in 15 ml isopropanol. To this, 0.3074 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour. The resulting product was insoluble in isopropanol and in water:isopropanol mixtures.

Example 16

A silicone urea triblock copolymer was synthesized by combining 0.3612 grams dipiperidyl propane (1.7 mmole, Sigma Aldrich, Milwaukee, WI) and 0.1891 grams of Jeffamine ED600 (0.3 mmole, Sigma Aldrich, Milwaukee, WI) in 15 ml isopropanol. To this, 0.3126 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour. The resulting product was insoluble in isopropanol and in water:isopropanol mixtures.

Example 17. Passivation Via Direct ELISA Assay

To 16 wells each in a 96-well plate, 100 uL of 1× phosphate buffered saline (PBS, Gibco/ThermoFisher, Grand Island, NY), 100 uL of 10 ug/ml goat IgG (Lampire Biological, Pipersville, PA) in PBS, and 100 uL of 10 ug/ml Rabbit IgG (Lampire Biological, Pipersville, PA) in PBS was added. The plate with the filled wells was shaken orbitally at room temperature for one hour in the dark to adsorb the IgG to the well surfaces. After one hour, the wells were all washed twice with PBS. To 4 of each type of coated well (none, goat IgG, or Rabbit IgG), 125 uL of PBS was added. To 4 of each type of coated well (none, goat IgG, or Rabbit IgG), 125 uL of 1% BSA (bovine serum albumin, Sigma Aldrich, St. Louis, MO) in PBS was added. To 4 of each type of coated well (none, goat IgG, or Rabbit IgG), 125 uL of a solution of silicone polyurea block copolymer prepared as described in Example 4 or Example 2 diluted to 1:100 in PBS, was added. The 96 well plate was orbitally shaken at room temperature in the dark for one hour.

After one hour, all wells were washed twice with PBS, then 75 uL of a 1:100,000 dilution of mouse anti-rabbit IgG-horseradish peroxidase (Sigma Aldrich, St. Louis, MO) in PBS was added to each well. The 96 well plate was then orbitally shaken at room temperature in the dark for one hour. After one hour, the wells were all rinsed twice with PBS, the plate was inverted to remove any remaining solution, then 50 ul/well of TMB developing solution (KPL/Seracare, Milford, MA) was added and the plate was orbitally shaken at room temperature in the dark for 10 minutes. After 10 minutes, 50 ul/well of 0.5N sulfuric acid was added to stop the reaction, and the optical density of the solutions in each well was measured at 450 nm. Results of the experiment in triplicate were averaged and normalized with the no primary antibody/no blocker condition as 1.0. Results demonstrated that the blocker from Example 4 performed statistically equivalent to BSA.

TABLE 1

| 1° Ab/Ag | Blocker | Ave A450 | St. Dev |
|---|---|---|---|
| none | none | 1.000 | 0.000 |
| GtIgG | none | 0.242 | 0.030 |
| RbIgG | none | 0.920 | 0.108 |
| none | BSA | 0.017 | 0.004 |
| GtIgG | BSA | 0.035 | 0.059 |
| RbIgG | BSA | 0.825 | 0.122 |
| none | Example 4 | 0.039 | 0.011 |
| GtIgG | Example 4 | 0.025 | 0.005 |
| RbIgG | Example 4 | 0.843 | 0.091 |
| none | Example 2 | 0.377 | 0.128 |
| GtIgG | Example 2 | 0.001 | 0.008 |
| RbIgG | Example 2 | 0.642 | 0.292 |

Example 18. Cell Passivation

The copolymer solution of Example 4 was serially diluted from 1:10 to 1:2430 in isopropanol. From each diluted solution, 100 uL per well was added to a 24 well tissue-culture polystyrene plate. The solutions dwelled in the wells for at least 1 minute, then were aspirated, and the coated 24-well plate was dried overnight in a class II laminar flow biosafety cabinet (Thermoscientific 1300 Series A2, Waltham, MA). After 18 hours, the wells were all rinsed three times with 1 mL of cell culture grade water (Sigma Aldrich, St. Louis, MO) and air dried in the biosafety cabinet.

Human dermal fibroblast cells (neonatal foreskin, ATCC PCS201010, American Type Culture Collection, Manassas, VA) were seeded into each well and into uncoated control wells at 48,000 cells per well in 1 mL of fibroblast media with a composition of Fibroblast basal media (part PCS201030, American Type Culture Collection, Manassas, VA) supplemented with 2% fetal bovine serum (Gibco/Thermofisher, Grand Island, NY) and fibroblast growth kit (part PCS201040, American Type Culture Collection, Manassas, VA) per manufacturer's instructions. The cells in the plate were incubated at 37° C. for 24 hours, then imaged with brightfield microscopy to determine the passivation level of the coatings by the number of adherent cells per well versus adherent cells in uncoated wells. The cell suspension of the supernatant of the coated wells was also extracted, placed in a fresh 24 well tissue culture polystyrene plate, incubated for 24 hours at 37° C., then imaged with brightfield microscopy to determine if the coatings were cytotoxic.

Results indicated the coating was non-cytototoxic, as evidenced by healthy cells growing in the supernatant. The coated wells showed no cell adherence at 10 and 30 fold dilutions, a reduction of approximately 50-80% in cell adherence at 90 and 270 fold dilutions, and little reduction in cell adherence at 810-2430 fold dilution of the silicone polyurea copolymer synthesized in Example 4. Uncoated tissue-culture polystyrene wells (control) displayed standard fibroblast cell growth as expected.

Example 19. Coating Magnetic Microspheres with Silicone Polyurea

Three vials of 0.1 ml of 100 mg/ml Dynal MyOne Tosyl magnetic microspheres were pelleted with a magnet and washed with 0.1 ml of deionized water. To the vials, was added either 0.1 ml of: (1) deionized water, (2) bovine serum albumin at 1% in deionized water, (3) a solution of 40 mg/ml of Example 4 in 80:20 deionized water:isopropanol. The vials were rotated end over end at 4° C. overnight in the dark. The microsphere suspensions were pelleted with a magnet and washed three times with 1×PBS (PBS, Gibco/ThermoFisher, Grand Island, NY). The microspheres samples are each suspended in 0.1 ml of 1×PBS in the final wash, then 0.5 ml of 10 ug/ml rabbit IgG (Lampire Biological, Pipersville, PA) in PBS was added, the vials were vortexed thoroughly and rotated end over end at room temperature for 1 hour in the dark. Each microsphere sample was washed three times with deionized water, then 0.5 ml of 1% BSA in deionized water was added, the sample vortexed, and rotated end over end at 4° C. overnight in the dark. The samples were then all washed with 1×PBS three times, transferred to new vials, and resuspended in mouse anti-rabbit IgG-horseradish peroxidase conjugate (Sigma Aldrich, St. Louis, MO) diluted 1:10,000 in PBS. Each microsphere sample was vortexed and rotated end over end for one hour at room temperature. After one hour, the magnetic microspheres were pelleted and washed three times with 1×PBS, and to each vial 0.25 ml of TMB developing solution (KPL/Seracare, Milford, MA) was added. Each vial was vortexed and rotated end over end for 15 minutes at room temperature, then 0.25 ml of 0.5N sulfuric acid was added to each vial to stop the color development, the microspheres were pelleted magnetically and the supernatant was extracted. The supernatant optical density was read at 450 nm, and the results normalized to the deionized water blocker condition.

TABLE 2

| Pre-Rabbit IgG Blocker | Post-Rabbit IgG Blocker | Ave A450 |
|---|---|---|
| None | BSA | 1.000 |
| BSA | BSA | 0.391 |
| Example 4 | BSA | 0.317 |

The silicone polyurea passivated against rabbit IgG adsorption and withstood all the magnetic pelleting, wash, and vortexing conditions (all pelleting was performed magnetically above). Results indicated the silicone polyurea copolymer coatings were quite durable on the microsphere surfaces.

Example 20. Silicone Polyurea

A silicone polyurea triblock copolymer was synthesized by combining 0.2971 grams dipiperidyl propane (1.4 mmole, Sigma Aldrich, Milwaukee, WI) and 0.3747 grams of Jeffamine ED600 (0.6 mmole, Sigma Aldrich, Milwaukee, WI) in 15 ml isopropanol. To this, 0.3134 grams monofunctional silicone isocyanate (MW~15,000, 0.02 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour. The resulting product was soluble in isopropanol and used without further purification.

Example 21. Silicone Polyurea

A silicone polyurea triblock copolymer was synthesized by combining 0.2957 grams dipiperidyl propane (1.4 mmole, Sigma Aldrich, Milwaukee, WI) and 0.3626 grams of Jeffamine ED600 (0.6 mmole, Sigma Aldrich, Milwaukee, WI) in 15 ml isopropanol. To this, 0.9114 grams monofunctional silicone isocyanate (MW~15,000, 0.06 mmoles, Silar, Wilmington, NC) was added with stirring for 15 minutes at room temperature, followed by the addition of 0.415 ml of hexane diisocyanate (2.6 mmoles, Sigma Aldrich, Milwaukee, WI). The reaction mixture was stirred vigorously at room temperature for 1 hour. The resulting product was soluble in isopropanol and used without further purification.

Example 22. Silicone Polyurea as Dry Lubricity

PEBAX rod (72 durometer, Minnesota MedTec, Maple Grove, MN) was cut into 4 inch long segments, then cleaned by wiping with isopropanol with a tex-wipe, then air dried. Pieces of PEBAX 72D rod stock were coated for each of the solutions by dipping the rod into a solution that is a 20% dilution of the coating solution made in Example 20 or Example 21 with isopropanol, dwelling in the solution for 30 seconds, then extracting at a speed of 0.5 cm/sec and air dried for 10 minutes. Lubricity of the coated pieces were tested with an HMS 5001 Friction Tester (Harland Medical Systems, Eden Prairie, MN) using 500 grams of normal force over 3 cm path length against stainless steel 304 foil tape on silicone pads (McMaster Carr, Chicago, IL). The coated pieces were tested dry without any liquid lubricant for 15 cycles and averaged over the pull. Coated pieces required less force to pull against stainless steel than uncoated PEBAX.

TABLE 3

| Sample | $1^{st}$ cycle average pull force in grams | $15^{th}$ cycle average pull force in grams |
|---|---|---|
| Uncoated PEBAX | 161.07 | 175.37 |
| Example 20 | 35.00 | 38.13 |
| Example 21 | 36.36 | 29.80 |

Results illustrate the reduction in the coefficient of friction observed in samples coated with silicone polyurea as compared to uncoated PEBAX.

Example 23. Bacterial Adherence Testing

Acrylic slides (Ted Pella, Inc. Redding, CA) were cleaned by wiping three times with isopropanol, air dried, and then dip coated with a 10 mg/ml solution of the silicone polyurea prepared in Example 5 or Example 7 in isopropanol. The slides remained in the coating solution for 30 seconds and then were extracted at a rate of 0.5 cm/sec. The coated slides were air dried for 15 minutes, and then illuminated for 2 minutes per side with UVB (306 nm) light to sterilize them.

The coated sterilized slides were then each placed in 10 ml of *E. coli* (DH5a, ATCC, Manassas, VA) in Luria-Bertani (LB) broth (MP Biomedical, Solon, OH, freshly seeded overnight and grown at 37° C., 100 rpm, with an OD adjusted to 0.5). The coated slides remained in the *E. coli* solution overnight at 37° C., 100 rpm. After the *E. coli* exposure, the slides were rinsed three times with 13 ml each of Butterfield's buffer for five minutes each. The rinsed slides were stained with 2 ml of safranin dye (1:5 concentration, PML Microbiologicals, Wilsonville, OR) for one minute, then rinsed with 2 ml of Butterfield's buffer for one minute. Slides were visualized by microscope (Leica, Buffalo Grove, IL) at 50× with a wet mount and ImageJ used to count the number of cells. At least six images per slide were taken and the number of bacteria per $mm^2$ averaged with one standard deviation reported in the table below.

TABLE 4

| Coating | *E. Coli* bacteria/$mm^2$ Average ± standard deviation |
|---|---|
| Uncoated Acrylic Slide | 2636 ± 2193 |
| Acrylic slide coated with Example 5 | 434 ± 455 |
| Acrylic slide coated with Example 7 | 46 ± 114 |

Results illustrated that slides coated with silicone polyurea copolymers in accordance with inventive principles demonstrated significantly reduced bacterial adherence as compared to uncoated slides.

Example 24. Material Properties of Silicone Polyurea

A silicone polyurea copolymer was synthesized as follows. 0.93 g of Jeffamine ED600 (1.6 mmole, Sigma Aldrich, Milwaukee, WI) and 84.8 mg dipiperidyl propane (0.4 mmole, Sigma Aldrich, Milwaukee, WI) was combined in 15 ml of isopropanol. To this, 0.1557 g of monofunctional silicone isocyanate (MW~15,000, 0.5 mmoles, Silar, Wilmington, NC) was added with stirring for 15 minutes at room temperature, followed by the addition of a solution of 0.415 ml of hexane diisocyanate (2.6 mmoles, Sigma Aldrich, Milwaukee, WI). The reaction mixture was stirred vigorously at room temperature for overnight, then used without further purification.

The prepared silicone polyurea, and the silicone polyurea from Example 5, were cast as films directly out of isopropanol reaction solvent onto a glass pan. After evaporation of the solvent, dogbone-shaped samples were cut out of the Example 5 film with a standardized die. The films were characterized on an Instron Universal Tester 3343 (Instron, Norwood MA) by elongating the sample until break at a rate of 1 mm/sec while measuring the force to generate stress-strain curves. From the curve, the Young's modulus and tensile strength were calculated as shown in the table below. Additionally, both films were tested for hardness with a digital Shore D durometer (Phase II model PHT-980, Phase II, Upper Saddle River, NJ) with at least three measurements. The average durometer in Shore D is recorded in the table below.

TABLE 5

| Sample | Young's modulus in psi | Tensile strength in psi | Shore D hardness |
|---|---|---|---|
| Silicone polyurea from Example 5 | 452 | 326 | 7D |
| Silicone polyurea this example | — | — | 17D |

Example 25. Photo Silicone Polyurea Copolymers

A photo-derivatized version of a silicone polyurea copolymer was synthesized by combining 310.2 mg of Jeffamine ED600 (0.5 mmole, Sigma Aldrich, Milwaukee, WI) and 274.6 mg dipiperidyl propane (1.3 mmole, Sigma Aldrich, Milwaukee, WI) in 10 ml of isopropanol. To this, 302.1 mg monofunctional silicone isocyanate (MW~15,000, 0.1 mmoles, Silar, Wilmington, NC) was added with stirring for 15 minutes at room temperature, followed by the addition of a solution of 45.4 mg of 4,4'-diaminobenzophenone (0.2 mmole, Sigma Aldrich, Milwaukee, WI) dissolved in 5 mL of methanol and 0.50 ml of isophorone diisocyanate (2.4 mmoles, Sigma Aldrich, Milwaukee, WI). The reaction mixture was stirred vigorously at room temperature overnight, then used without further purification.

Example 26. Silicone Polyurea Copolymer

A silicone polyurea triblock copolymer was synthesized by combining 1.75 grams of Jeffamine ED600 (3 mmole, Sigma Aldrich, Milwaukee, WI) and 1.9042 grams monofunctional silicone isocyanate (MW~15,000, 0.15 mmoles, Silar, Wilmington, NC) in 15 ml of isopropanol. The reaction mixture was stirred for 15 minutes at room temperature, after which 0.48 ml of hexane diisocyanate (3 mmoles, Sigma Aldrich, Milwaukee, WI) was added. The reaction mixture was stirred vigorously at room temperature for 1 hour, then used without further purification.

The invention claimed is:

1. A non-implanted medical device having a surface containing a passivating coating, the passivating coating comprising a silicone polyurea copolymer having a polymer backbone and comprising a reaction product of:

(a) a diamine composition comprising a polyethylene glycol diamine compound having a formula (I), (II), or a combination of (I) and (II):

(I)

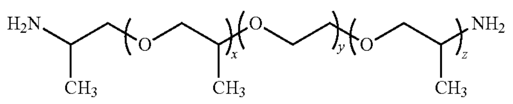

wherein y is an integer in the range of 2 to 40, and x+z is an integer in the range of 1 to 8; or (II)

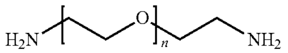

wherein n is an integer in the range of 1 to 100;

(b) a monofunctional silicone isocyanate compound having a formula:

(VIII)

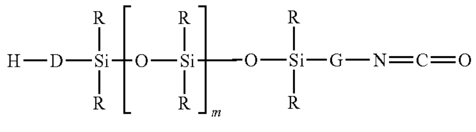

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (c) a diisocyanate compound, wherein the silicone polyurea copolymer comprises total isocyanate groups to total amine groups in a molar ratio of 1.5:1 to 1.05:1.

2. The non-implanted medical device of claim 1 selected from laboratory plates, tubes, trays, capillaries, and containers; diagnostic slides; chromatographic support materials; cell culture ware; biosensors; and microfluidic devices.

3. The non-implanted medical device of claim 1 selected from transdermal drug delivery devices, dialysis devices and dialysis tubing, catheters, membranes and grafts, autotransfusion devices, intraaortic balloon pumps, intracardiac suction devices, blood pumps, blood oxygenator devices, blood filters, blood temperature monitors, hemoperfusion units, plasmapheresis units, transition sheaths, dialators, intrauterine pressure devices, breathing circuit connectors, stylets, guidewires, dialators, surgical instruments, endoscopic devices, hearing aids, blood storage bags, umbilical tape, membranes, wound dressings, wound management devices, needles, percutaneous closure devices, transducer protectors, uterine bleeding patches, clamps, cannulae.

4. The non-implanted medical device of claim 1 wherein the polyethylene glycol diamine compound has a molecular weight of 100 to 4,434.

5. The non-implanted medical device of claim 1 wherein the diamine composition of (a) further comprises a dipiperidyl alkane, and wherein the diamine composition comprises 20 to 99.9 molar percent of the polyethylene glycol and 0.1 to 80 molar percent of the dipiperidyl alkane.

6. The non-implanted medical device of claim 5 wherein the dipiperidyl alkane has a formula:

(VI)

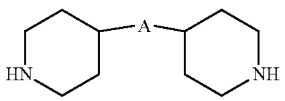

where A is a C0 to C 8 bivalent radical.

7. The non-implanted medical device of claim 6 wherein the dipiperidyl alkane comprises dipiperidyl propane.

8. The non-implanted medical device of claim 1 wherein the silicone isocyanate has a molecular weight in a range of 1,000 to 20,000.

9. The non-implanted medical device of claim 1 wherein the diisocyanate has a formula:

OCN—B—NCO (VII)

where B is a bivalent alkyl radical having 2 to 20 carbon atoms.

10. The non-implanted medical device of claim 9, wherein the diisocyanate is selected from hexane diisocyanate and isophorone diisocyanate.

11. The non-implanted medical device of claim 1 wherein the copolymer comprises polyethylene glycol in amount of 25 to 95 weight percent, based on total weight of the silicone polyurea copolymer.

12. The non-implanted medical device of claim 1 wherein the silicone polyurea copolymer has a Hardness Value of 30 D or less.

13. The non-implanted medical device of claim 1 wherein the silicone polyurea copolymer has an average molecular weight of 100,000 or less.

14. The non-implanted medical device of claim 1 wherein the silicone polyurea copolymer further comprises one or more latent reactive groups selected from a photoreactive group, a thermally reactive group, a chemically reactive group, or a combination of any two or more of these.

15. A medical device fabricated of a material selected from silicone, polystyrene, polyethylene terephthalate, polyethylene, polyvinyl chloride, polypropylene, polyurethane, polytetrafluoroethylene, polyamide, polyolefin, or copolymers or combinations thereof, the device having a surface containing a dry lubricious coating, the dry lubricious coating comprising a silicone polyurea copolymer having a polymer backbone and comprising a reaction product of:

(a) a diamine composition comprising a polyethylene glycol diamine compound having a formula (I), (II), or a combination of (I) and (II):

(I)

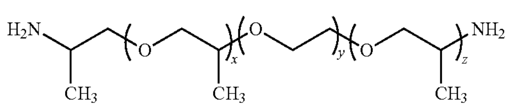

wherein y is an integer in the range of 2 to 40, and x+z is an integer in the range of 1 to 8; or (II)

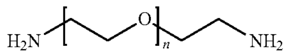

wherein n is an integer in the range of 1 to 100;

(b) a monofunctional silicone isocyanate compound having a formula:

(VIII)

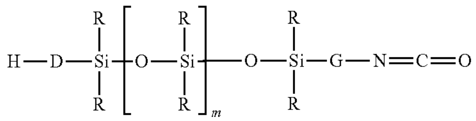

wherein D is an alkyl radical having 1 to 6 carbon atoms, G is a bivalent alkyl radical having 1 to 6 carbon atoms, each R is independently selected from a monovalent alkyl radical having about 1 to about 12 carbon atoms, a substituted alkyl radical having about 1 to about 12 carbon atoms, a phenyl radical and a substituted phenyl radical, and m is an integer in the range of 15 to 300; and (c) a diisocyanate compound, wherein the silicone polyurea copolymer comprises total isocyanate groups to total amine groups in a molar ratio of 1.5:1 to 1.05:1, wherein the dry lubricous coating provides the medical device with reduced frictional resistance against an uncoated substrate as compared to an uncoated medical device or medical article.

16. The medical device of claim 15 wherein the dry lubricous coating provides frictional resistance that is at least 50% less than frictional resistance of an uncoated medical device or medical article.

17. The medical device of claim 15 wherein the diamine composition of (a) further comprises a dipiperidyl alkane, and wherein the diamine composition comprises 20 to 99.9 molar percent of the polyethylene glycol and 0.1 to 80 molar percent of the dipiperidyl alkane.

18. The medical device of claim 17 wherein the dipiperidyl alkane comprises dipiperidyl propane.

19. The medical device of claim 15 wherein the diisocyanate has a formula:

OCN—B—NCO (VII)

where B is a bivalent alkyl radical having 2 to 20 carbon atoms.

20. The medical device of claim 19, wherein the diisocyanate is selected from hexane diisocyanate and isophorone diisocyanate.

* * * * *